(12) United States Patent
Leem et al.

(10) Patent No.: US 9,991,174 B2
(45) Date of Patent: Jun. 5, 2018

(54) METHOD AND SYSTEM OF MEASURING SEMICONDUCTOR DEVICE AND METHOD OF FABRICATING SEMICONDUCTOR DEVICE USING THE SAME

(71) Applicants: Choonshik Leem, Seoul (KR); Jihye Lee, Suwon-si (KR); Deokyong Kim, Gunpo-si (KR); Soobok Chin, Seoul (KR)

(72) Inventors: Choonshik Leem, Seoul (KR); Jihye Lee, Suwon-si (KR); Deokyong Kim, Gunpo-si (KR); Soobok Chin, Seoul (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 655 days.

(21) Appl. No.: 14/520,477

(22) Filed: Oct. 22, 2014

(65) Prior Publication Data

US 2015/0206806 A1     Jul. 23, 2015

(30) Foreign Application Priority Data

Jan. 17, 2014    (KR) ........................ 10-2014-0005979

(51) Int. Cl.

| | |
|---|---|
| *G01N 21/47* | (2006.01) |
| *H01J 37/28* | (2006.01) |
| *H01L 21/66* | (2006.01) |
| *G01N 21/95* | (2006.01) |
| *G01N 21/956* | (2006.01) |

(52) U.S. Cl.
CPC ......... *H01L 22/12* (2013.01); *G01N 21/9501* (2013.01); *G01N 21/95607* (2013.01); *G01N 21/95684* (2013.01); *H01J 37/28* (2013.01); *G01B 2210/56* (2013.01); *H01J 2237/24578* (2013.01); *H01J 2237/24592* (2013.01)

(58) Field of Classification Search
CPC ............ H01L 22/12; H01L 2924/0002; H01L 27/10876; G03F 7/70625; G03F 7/70633; G01N 21/9501
USPC ......... 257/E21.09, E21.19; 438/14, 270, 283
See application file for complete search history.

(56) References Cited

U.S. PATENT DOCUMENTS

| | | | |
|---|---|---|---|
| 6,742,168 B1 | 5/2004 | Nariman | |
| 7,139,083 B2 * | 11/2006 | Fielden | ................ G01N 21/211 |
| | | | 257/E21.53 |
| 7,710,579 B2 | 5/2010 | Yamaguchi et al. | |

(Continued)

FOREIGN PATENT DOCUMENTS

| | | |
|---|---|---|
| JP | 2000252339 A | 9/2000 |
| JP | 2001-082931 A | 3/2001 |

(Continued)

*Primary Examiner* — Roy Y Yi
*Assistant Examiner* — Jeffrey Aiello
(74) *Attorney, Agent, or Firm* — Harness, Dickey & Pierce, P.L.C.

(57) ABSTRACT

The measurement method may include obtaining first measurement data from a recess region formed in a semiconductor substrate, obtaining second measurement data from a conductive pattern filling a portion of the recess region, calculating a first volume of the recess region from the first measurement data, calculating a second volume of the conductive pattern from the second measurement data, and calculating a measurement target parameter using a difference between the first and second volumes.

8 Claims, 21 Drawing Sheets

(56) References Cited

U.S. PATENT DOCUMENTS

| | | | |
|---|---|---|---|
| 8,649,016 B2 | 2/2014 | Marx et al. | |
| 2002/0103564 A1* | 8/2002 | Fielden | G01N 21/211 700/121 |
| 2004/0087041 A1* | 5/2004 | Perry | G01B 11/0616 438/5 |
| 2004/0235205 A1* | 11/2004 | Levy | G01N 21/211 438/14 |
| 2006/0287754 A1* | 12/2006 | Sugamoto | G05B 19/41875 700/121 |
| 2007/0264810 A1* | 11/2007 | Kim | H01L 21/28061 438/585 |
| 2008/0049222 A1 | 2/2008 | Yamaguchi et al. | |
| 2009/0084759 A1* | 4/2009 | MacCrimmon | H01J 37/3023 216/84 |
| 2009/0122321 A1* | 5/2009 | Rosenthal | G01B 11/0625 356/496 |
| 2011/0125458 A1 | 5/2011 | Xu et al. | |
| 2011/0229988 A1* | 9/2011 | Asano | B82Y 10/00 438/7 |
| 2011/0272789 A1* | 11/2011 | Wang | B01L 3/502707 257/618 |
| 2011/0292375 A1 | 12/2011 | Marx et al. | |
| 2012/0217392 A1* | 8/2012 | Murakawa | G01B 15/00 250/307 |
| 2013/0051530 A1* | 2/2013 | Nepomnishy | G21K 1/025 378/85 |
| 2013/0077742 A1 | 3/2013 | Schueler et al. | |
| 2013/0140516 A1* | 6/2013 | Lee | H01L 27/2463 257/5 |
| 2015/0377801 A1* | 12/2015 | Sugimoto | G01N 23/083 378/54 |

FOREIGN PATENT DOCUMENTS

| | | |
|---|---|---|
| JP | 2007-335557 A | 12/2007 |
| JP | 2011-192769 A | 9/2011 |
| KR | 10-2013-0010881 A | 1/2013 |

* cited by examiner

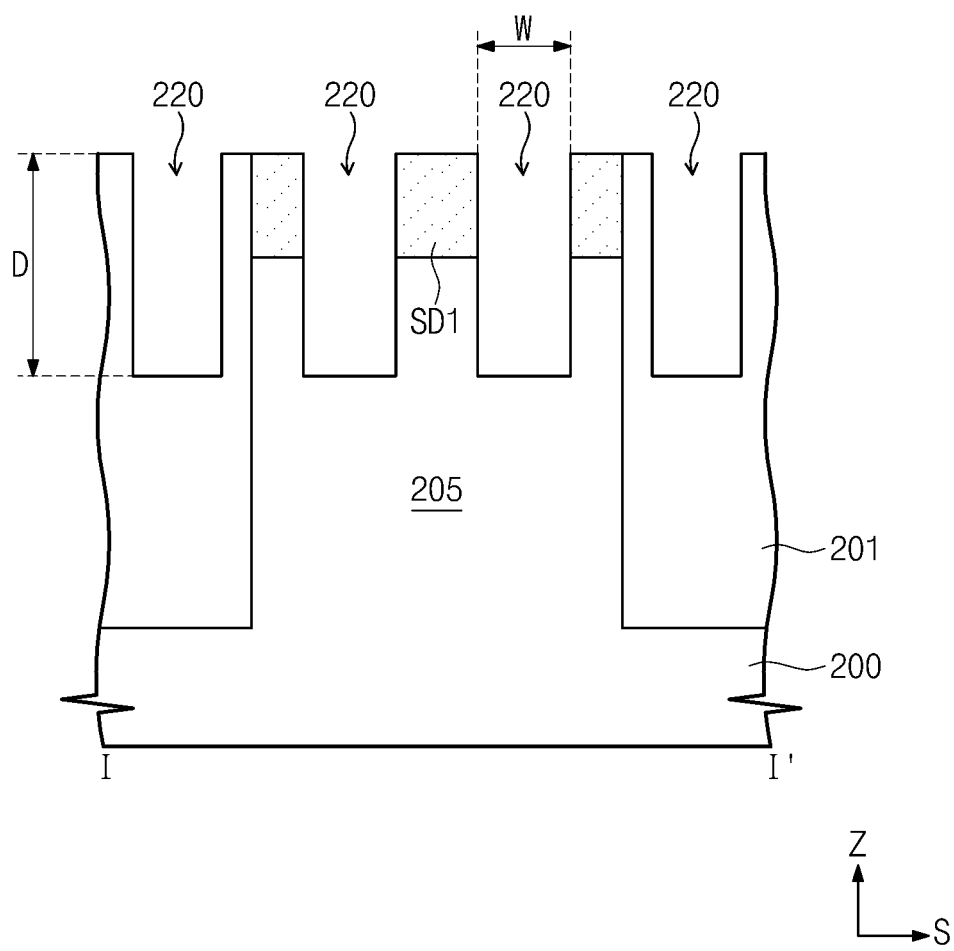

METHOD AND SYSTEM OF MEASURING SEMICONDUCTOR DEVICE AND METHOD OF FABRICATING SEMICONDUCTOR DEVICE USING THE SAME

CROSS-REFERENCE TO RELATED APPLICATIONS

This U.S. non-provisional patent application claims priority under 35 U.S.C. § 119 to Korean Patent Application No. 10-2014-0005979, filed on Jan. 17, 2014, in the Korean Intellectual Property Office, the entire contents of which are hereby incorporated by reference.

BACKGROUND OF THE INVENTION

Example embodiments of the inventive concepts relate to a method of and a system for measuring a semiconductor device and/or a method of fabricating a semiconductor device using the same.

Due to their small-sized, multifunctional, and/or low-cost characteristics, semiconductor devices are important elements in the electronic industry. Semiconductor devices may be fabricated using various processes such as photolithography, etching, deposition, ion implantation, and cleaning processes.

A measurement process is performed to examine whether there is any failure in patterns constituting a fabricated semiconductor device. By performing the measurement process, it is possible to optimize a process condition of the fabrication process and know whether there is any failure in a semiconductor device in an early stage.

As the semiconductor device is scaled down, there is an increasing demand for a method and a system capable of reliably measuring fine patterns in the semiconductor device.

SUMMARY

Some example embodiments of the inventive concepts provide a method and/or a system capable of measuring a semiconductor device with improved reliability.

Some other example embodiments of the inventive concepts provide a method and/or a system capable of reducing a process time taken to measure a semiconductor device.

Still other example embodiments of the inventive concepts provide a method of fabricating a semiconductor device with high reliability.

According to example embodiments, a method of measuring a semiconductor device may include obtaining, using a first measurement instrument, first measurement data from a recess region formed in a semiconductor substrate, obtaining, using a second measurement instrument, second measurement data from a conductive pattern filling a portion of the recess region, obtaining, using a controller, a first volume of the recess region from the first measurement data, obtaining, using a controller, a second volume of the conductive pattern from the second measurement data, and obtaining, using a controller, a measurement target parameter using a difference between the first and second volumes.

In an example embodiment, the recess region may include a lower region adjacent to a bottom surface of the recess region and an upper region separated from the bottom surface of the recess region, the conductive pattern fills the lower region, and the measurement target parameter may be a distance between a top surface of the conductive pattern and a top surface of the semiconductor substrate.

In an example embodiment, the obtaining the first measurement data may include measuring a width of the recess region and measuring a depth of the recess region.

In an example embodiment, the recess region may be a line-shaped trench extending along a specific direction, the width of the recess region may be a distance between opposing sidewalls of the semiconductor substrate defining the trench, and the depth of the recess region may be a distance between a bottom surface of the trench and a top surface of the semiconductor substrate.

In an example embodiment, the recess region may have a hole-shaped structure extending into at least a portion of the semiconductor substrate, the width of the recess region may be a diameter of the hole, and the depth of the recess region may be a distance between a bottom surface of the hole and a top surface of the semiconductor substrate.

In an example embodiment, the obtaining the first volume comprises calculating the first volume by multiplying the width of the recess region, the depth of the recess region, and a first constant.

In an example embodiment, the obtaining the second measurement data may include measuring a mass of an element contained in the conductive pattern.

In an example embodiment, the obtaining the second volume comprises calculating the second volume by multiplying the mass of the element contained in the conductive pattern by a second constant.

In an example embodiment, the comprises the measurement target parameter comprises calculating the measurement target parameter dividing a third volume, which is obtained by subtracting the second volume from the first volume, by multiplication of the width of the recess region and the first constant.

In an example embodiment, a side surface of the recess region may have a slanted profile, and the obtaining the first volume of the recess region may include correcting a measurement value of the depth to be approximately same as an actual value of the depth.

In an example embodiment, the method may further include verifying a calculation of the measurement target parameter, the verifying includes obtaining reference data, and correcting a calculation data for the measurement target parameter to reduce an error between the measurement target parameter and the reference data.

In an example embodiment, if the calculation module may be corrected, the calculating the measurement target parameter may be performed again using the corrected calculation data.

In an example embodiment, the conductive pattern may include a metal material.

According to another example embodiment, a system for measuring a semiconductor device may include a first measurement instrument configured to measure a width of a recess region formed in a semiconductor substrate, a second measurement instrument configured to measure a depth of the recess region, a third measurement instrument configured to measure mass of an element contained in a conductive pattern filling a portion of the recess region, and a computer system configured to calculate a first volume of the recess region using the width and the depth of the recess region, calculate a second volume of the conductive pattern using the mass of the element contained in the conductive pattern, and calculate a measurement target parameter using a difference between the first and second volumes.

In an example embodiment, the computer system may include a calculation module configured to calculate the measurement target parameter, and the calculation module may be configured to calculate the first volume, the second volume, and the measurement target parameter. The first volume may be calculated by multiplying the width of the recess region, the depth of the recess region, and a first constant, the second volume may be calculated by multiplying the mass of the element contained in the conductive pattern by a second constant, and the measurement target parameter may be calculated by dividing a third volume, which is obtained by subtracting the second volume from the first volume, by multiplication of the width of the recess region and the first constant.

In an example embodiment, the computer system may further include a verification module configured to verify the calculation module, and the verification module may be configured to determine the first and second constants to reduce an error between the measurement target parameter calculated by the calculation module and reference data.

In an example embodiment, the first measurement instrument may be a scanning electron microscope (SEM) instrument, the second measurement instrument may be an optical scatterometry instrument, and the third measurement instrument may be an X-ray fluorescence analysis instrument.

In an example embodiment, the computer system may include a measurement controller, and the first, second, and third measurement instruments may be controlled by the measurement controller.

According to some other example embodiments, a method of fabricating a semiconductor device may include forming a device isolation layer on a substrate to define an active pattern, etching the active pattern and the device isolation layer to form a trench crossing the active pattern, obtaining first measurement data from the trench, forming a gate pattern in the trench to cross the active pattern and be buried in the substrate, obtaining second measurement data from the gate pattern, obtaining a first volume of the trench using the first measurement data, obtaining a second volume of the gate pattern using the second measurement data, obtaining a measurement target parameter using a difference between the first and second volumes, and examining whether the measurement target parameter is within an allowed range.

In an example embodiment, the trench may include a lower region adjacent to a bottom surface of the trench and an upper region separated from the bottom surface, the gate pattern fills the lower region, and the measurement target parameter may be a distance between a top surface of the gate pattern and a top surface of the substrate.

In an example embodiment, the obtaining the first measurement data may include measuring a width of the trench and measuring a depth of the trench.

In an example embodiment, the first measurement data may be obtained using a non-destructive testing method, the width of the trench may be measured by a scanning electron microscope (SEM) instrument, and the depth of the trench may be measured by an optical scatterometry instrument.

In an example embodiment, the obtaining the second measurement data may include measuring mass of an element contained in the gate pattern.

In an example embodiment, the second measurement data may be obtained using a non-destructive testing method, and the mass of the element contained in the gate pattern may be measured by an X-ray fluorescence analysis instrument.

In an example embodiment, the obtaining the measurement target parameter may include operating a calculation module included in a computer system, the calculation module may be configured to calculate the first volume, the second volume, and the measurement target parameter, the first volume being calculated by multiplying the width of the trench, the depth of the trench, and a first constant, the second volume being calculated by multiplying the mass of the element contained in the gate pattern by a second constant, and the measurement target parameter being calculated by dividing a third volume, which is obtained by subtracting the second volume from the first volume, by multiplication of the width of the trench and the first constant.

In an example embodiment, the obtaining of the measurement target parameter may further include operating a verification module included in the computer system, the verification module may be configured to determine the first and second constants to reduce an error between the measurement target parameter calculated by the calculation module and reference data.

In an example embodiment, the gate pattern may include a metal material.

In an example embodiment, the forming of the gate pattern may include forming a gate layer on the substrate to fill the trench and etching the gate layer. If the examining determines the measurement target parameter may be smaller than the allowed range, repeating the etching process for forming the gate pattern.

In another embodiment, a method of determining a physical parameter of a semiconductor device under manufacture includes performing non-destructive measuring of at least first and second physical parameters of structures in the semiconductor device under manufacture using two different measurement instruments, and determining a third physical parameter of the structures based on data generated from the performing.

In one embodiment, the data generated from the performing includes a depth of a recess formed in a substrate and a mass of a material partially filling the recess; and the determining determines a distance from a top surface of the material to a top surface of the substrate.

BRIEF DESCRIPTION OF THE DRAWINGS

Example embodiments will be more clearly understood from the following brief description taken in conjunction with the accompanying drawings. The accompanying drawings represent non-limiting, example embodiments as described herein.

FIGS. 13A through 17A are plan views illustrating a method of fabricating a semiconductor device according to the further example embodiment of the inventive concepts.

FIGS. 13B through 17B are sectional views taken along line I-I' of FIGS. 13A through 17A, respectively.

Figure 1:
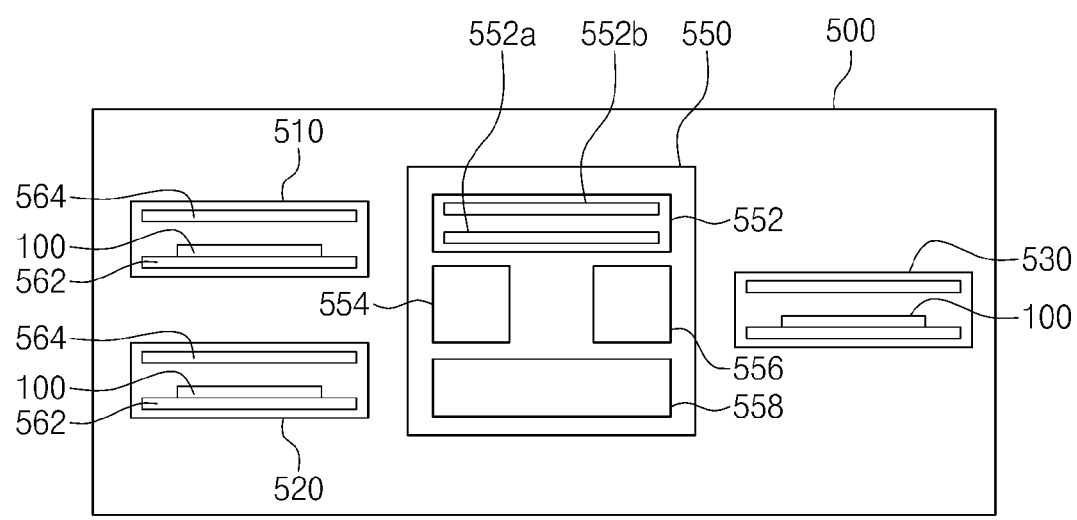
FIG. 1 is a schematic diagram illustrating a semiconductor measurement system according to an example embodiment of the inventive concepts.

It should be noted that these figures are intended to illustrate the general characteristics of methods, structure and/or materials utilized in certain example embodiments and to supplement the written description provided below. These drawings are not, however, to scale and may not precisely reflect the precise structural or performance characteristics of any given embodiment, and should not be interpreted as defining or limiting the range of values or properties encompassed by example embodiments. For example, the relative thicknesses and positioning of molecules, layers, regions and/or structural elements may be reduced or exaggerated for clarity. The use of similar or identical reference numbers in the various drawings is intended to indicate the presence of a similar or identical element or feature.

DETAILED DESCRIPTION

Example embodiments of the inventive concepts will now be described more fully with reference to the accompanying drawings, in which example embodiments are shown. Example embodiments of the inventive concepts may, however, be embodied in many different forms and should not be construed as being limited to the embodiments set forth herein; rather, these embodiments are provided so that this disclosure will be thorough and complete, and will fully convey the concepts of example embodiments to those of ordinary skill in the art. In the drawings, the thicknesses of layers and regions are exaggerated for clarity. Like reference numerals in the drawings denote like elements, and thus their description will be omitted.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Like numbers indicate like elements throughout. As used herein the term "and/or" includes any and all combinations of one or more of the associated listed items. Other words used to describe the relationship between elements or layers should be interpreted in a like fashion (e.g., "between" versus "directly between," "adjacent" versus "directly adjacent," "on" versus "directly on").

It will be understood that, although the terms "first", "second", etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of example embodiments.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

The terminology used herein is for the purpose of describing particular embodiments only and is not intended to be limiting of example embodiments. As used herein, the singular forms "a," "an" and "the" are intended to include the plural forms as well, unless the context clearly indicates otherwise. It will be further understood that the terms "comprises", "comprising", "includes" and/or "including," if used herein, specify the presence of stated features, integers, steps, operations, elements and/or components, but do not preclude the presence or addition of one or more other features, integers, steps, operations, elements, components and/or groups thereof.

Example embodiments of the inventive concepts are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments of the inventive concepts should not be construed as limited to the particular shapes of regions illustrated herein but are to include deviations in shapes that result, for example, from manufacturing. For example, an implanted region illustrated as a rectangle may have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature and their shapes are not intended to illustrate the actual shape of a region of a device and are not intended to limit the scope of example embodiments.

As appreciated by the present inventive entity, devices and methods of forming devices according to various embodiments described herein may be embodied in microelectronic devices such as integrated circuits, wherein a plurality of devices according to various embodiments described herein are integrated in the same microelectronic device. Accordingly, the cross-sectional view(s) illustrated herein may be replicated in two different directions, which need not be orthogonal, in the microelectronic device. Thus, a plan view of the microelectronic device that embodies devices according to various embodiments described herein may include a plurality of the devices in an array and/or in a two-dimensional pattern that is based on the functionality of the microelectronic device.

The devices according to various embodiments described herein may be interspersed among other devices depending on the functionality of the microelectronic device. Moreover, microelectronic devices according to various embodiments described herein may be replicated in a third direction that may be orthogonal to the two different directions, to provide three-dimensional integrated circuits.

Accordingly, the cross-sectional view(s) illustrated herein provide support for a plurality of devices according to various embodiments described herein that extend along two different directions in a plan view and/or in three different directions in a perspective view. For example, when a single active region is illustrated in a cross-sectional view of a device/structure, the device/structure may include a plurality of active regions and transistor structures (or memory cell structures, gate structures, etc., as appropriate to the case) thereon, as would be illustrated by a plan view of the device/structure.

Unless otherwise defined, all terms (including technical and scientific terms) used herein have the same meaning as commonly understood by one of ordinary skill in the art to which example embodiments of the inventive concepts belong. It will be further understood that terms, such as those defined in commonly-used dictionaries, should be interpreted as having a meaning that is consistent with their meaning in the context of the relevant art and will not be interpreted in an idealized or overly formal sense unless expressly so defined herein.

FIG. 1 is a schematic diagram illustrating a semiconductor measurement system according to example embodiments of the inventive concepts.

Referring to FIG. 1, a semiconductor measurement system 500 may include parameter measurement instruments 510, 520, and 530 and a computer system 550. The parameter measurement instruments may include a first measurement instrument 510, a second measurement instrument 520, and a third measurement instrument 530. Each of the parameter measurement instruments 510, 520, and 530 may include a chuck 562, on which a semiconductor substrate 100 is loaded, and a measuring unit 564 measuring parameter(s) of patterns formed on the semiconductor substrate 100. The first, second, and third measurement instruments 510, 520, and 530 may be configured to perform a non-destructive testing process. For example, the first measurement instrument 510 may be a scanning electron microscope (SEM) instrument, and the second measurement instrument 520 may be an optical scatterometry instrument. The third measurement instrument 530 may be an X-ray fluorescence analysis instrument.

The computer system 550 may include a controller 552 capable of processing various data and a memory device 554 capable of storing various data. The controller 552 may be configured to process parameter data obtained from the parameter measurement instruments 510, 520, and 530.

The controller 552 may include a calculator 552a processing the parameter data. In example embodiments, the controller 552 may further include a measurement controller 552b that is configured to control the measuring unit 564 of each of the parameter measurement instruments 510, 520, and 530. The measurement controller 552b may be configured to decide whether to measure parameters of patterns formed on the semiconductor substrate 100, to know whether the parameters of the patterns are precisely measured, and to decide whether to collect the parameter data measured by the measuring unit(s) 564. In this case, the parameter measurement instruments 510, 520, and 530 may be controlled by the computer system 550. However, in other example embodiments, the controller 552 may not include the measurement controller 552b, and in this case, the computer system 550 and the parameter measurement instruments 510, 520, and 530 may be devices, each of which can be independently and individually controlled.

The memory device 554 may include a nonvolatile memory device. For example, the memory device 554 may include a hard disk and/or a nonvolatile semiconductor memory device (e.g., a FLASH memory device, a phase-changeable memory device, and/or a magnetic memory device).

In addition, the computer system 550 may further include an input/output unit 556 and an interface unit 558. The input/output unit 556 may include a keyboard, a keypad, and/or a display device. Data obtained from the parameter measurement instruments 510, 520, and 530 may be transmitted to the computer system 550 through the interface unit 558. Further, data processed by the computer system 550 may be transmitted to the parameter measurement instruments 510, 520, and 530 through the interface unit 558. The interface unit 558 may include a wired element, a wireless element, and/or a universal serial bus (USB) port. The controller 552, the memory device 554, the input/output unit 556, and the interface unit 558 may be coupled to each other through a data bus.

The above semiconductor measurement system 500 may be used to perform a process of measuring a semiconductor device. Hereinafter, a measurement method of a semiconductor device according to some example embodiments of the inventive concepts will be described.

Figure 2A:
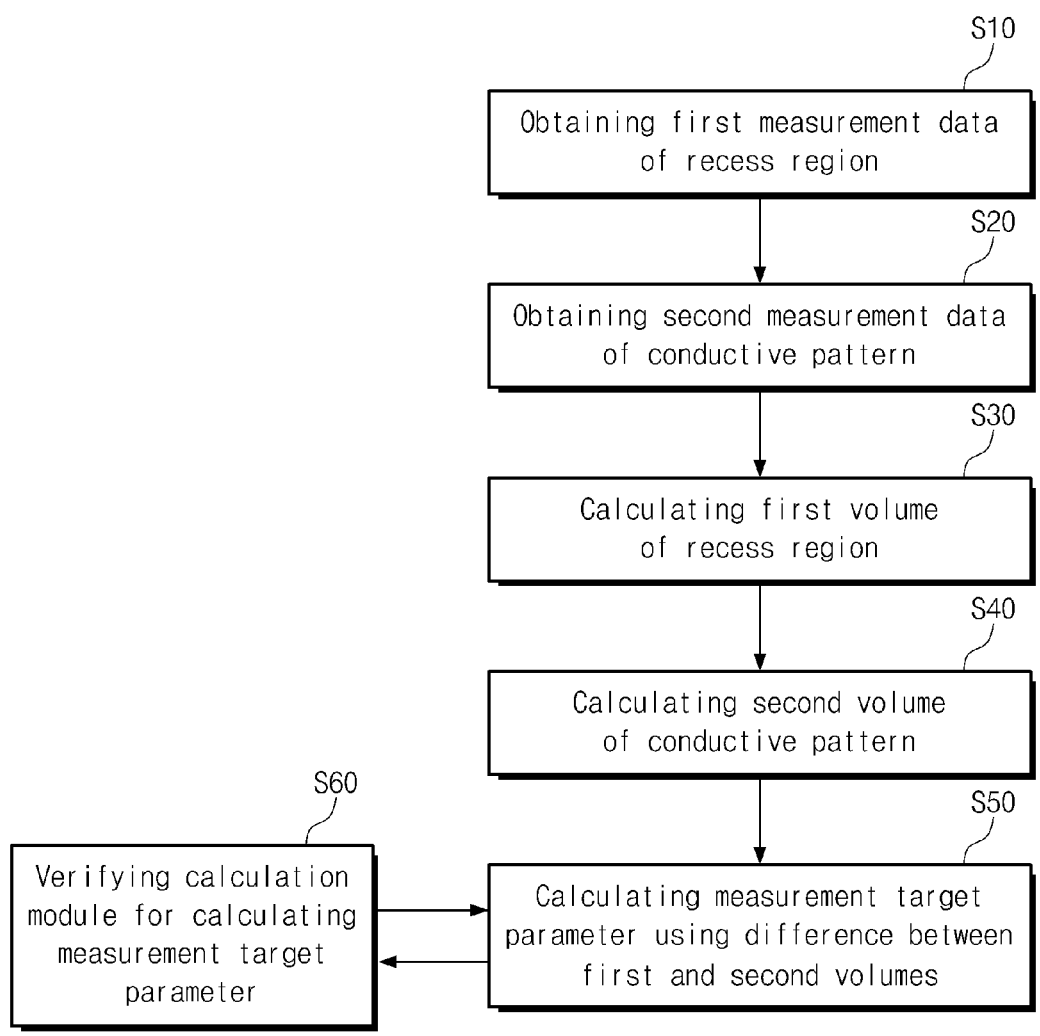
FIG. 2A is a flow chart illustrating a method of measuring a semiconductor device, according to an example embodiment of the inventive concepts.
Figure 2B:
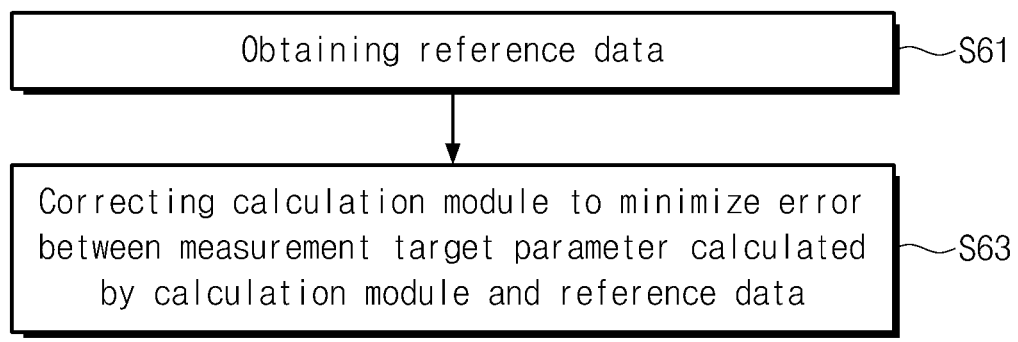
FIG. 2B is a flow chart illustrating a step S60 of FIG. 2A.
Figure 3:
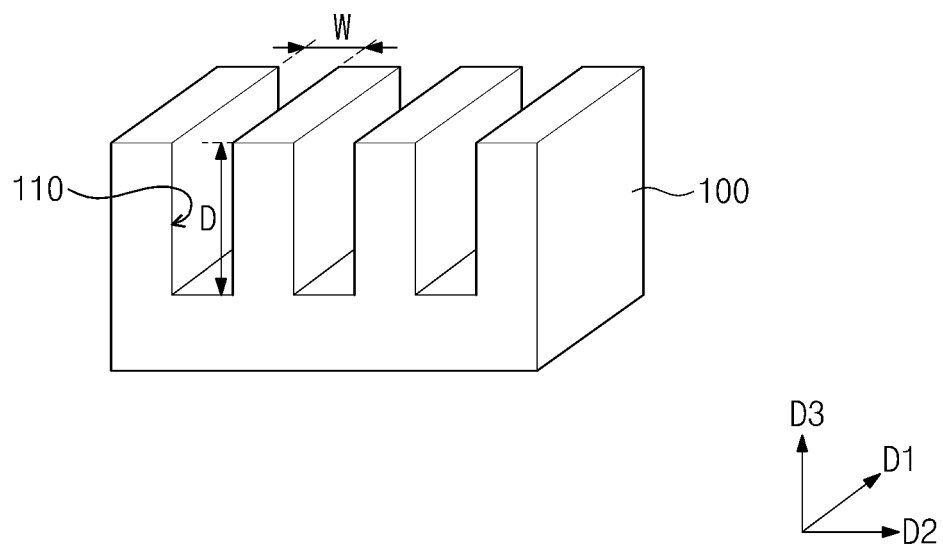
FIGS. 3 and 4 are perspective views illustrating a method of measuring a semiconductor device according to an example embodiment of the inventive concepts.
Figure 4:
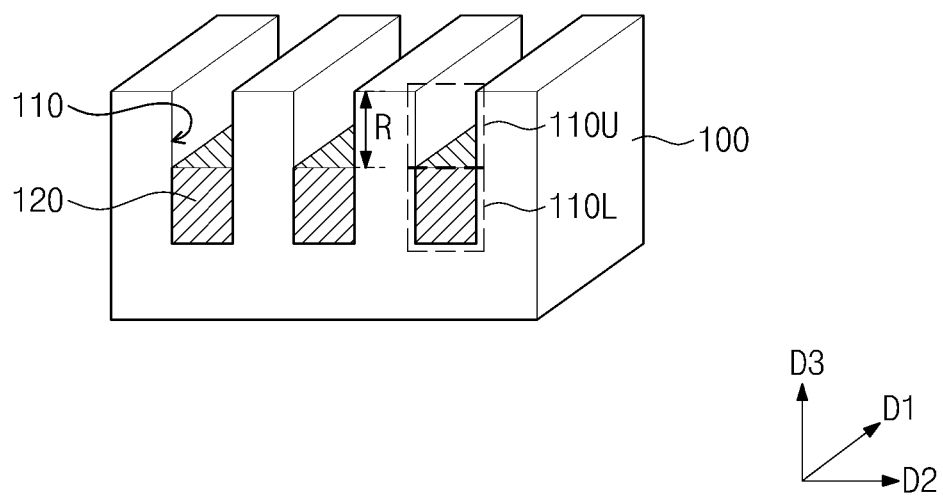
Figure 5:
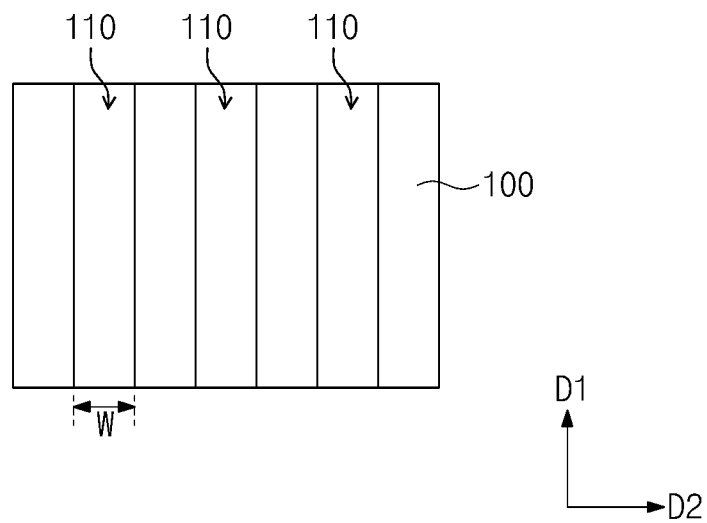
FIG. 5 is a plan view of FIG. 3.
Figure 6:
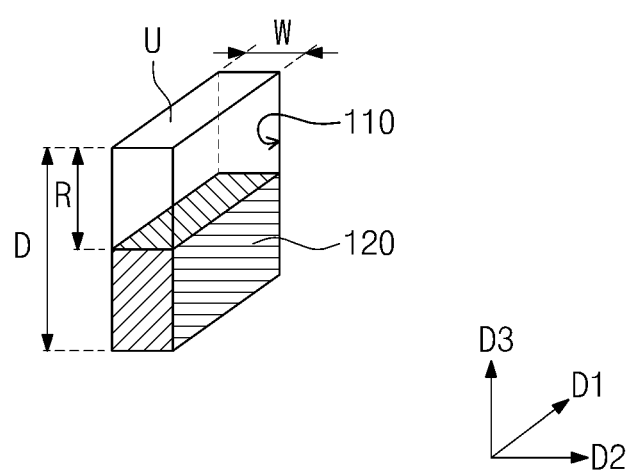
FIG. 6 is a geometrical model illustrating calculation parameters, which are used in a measurement method of a semiconductor device according to example embodiments of the inventive concepts.

FIG. 2A is a flow chart illustrating a method of measuring a semiconductor device, according to example embodiments of the inventive concepts, and FIG. 2B is a flow chart illustrating a step S60 of FIG. 2A. FIGS. 3 and 4 are perspective views illustrating a method of measuring a semiconductor device according to other example embodiments of the inventive concepts, and FIG. 5 is a plan view of FIG. 3. FIG. 6 is a geometrical model illustrating a calculation module, which is used in a measurement method of a semiconductor device according to an example embodiment of the inventive concepts.

First, referring to FIGS. 3 and 5, a plurality of recess regions 110 may be formed in a semiconductor substrate 100. The semiconductor substrate 100 may be, for example, a silicon wafer, a germanium wafer, or a silicon-germanium wafer. Although not illustrated, the semiconductor substrate 100 may include device isolation patterns defining active regions in the semiconductor substrate 100 and impurity injection regions formed in the active regions. According to the present embodiment, each of the recess regions 110 may be a line-shaped trench extending along a first direction D1. The recess regions 110 may be spaced apart from each other in a second direction D2 crossing the first direction D1.

Referring to FIGS. 1, 2A, 3, and 5, first measurement data of the recess region 110 may be obtained (in S10). The obtaining of the first measurement data may include measuring a width W of the recess region 110 and measuring a depth D of the recess region 110. In the present embodiment, the width W of the recess region 110 may be a distance between both side surfaces of the semiconductor substrate 100 defining the recess region 110. In addition, the depth D of the recess region 110 may be defined as a distance between a top surface of the semiconductor substrate 100 and a bottom surface of the recess region 110.

The width W of the recess region 110 may be measured using the first measurement instrument 510 of the semiconductor measurement system 500. For example, the semiconductor substrate 100 with the recess region 110 may be loaded on the chuck 562 of the first measurement instrument 510, and the width W may be measured using the measuring unit 564 of the first measurement instrument 510. The first measurement instrument 510 may be, for example, a scanning electron microscope (SEM) instrument. The depth D of the recess region 110 may be measured by the second measurement instrument 520 of the semiconductor measurement system 500. For example, the semiconductor substrate 100 with the recess region 110 may be loaded on the chuck 562 of the second measurement instrument 520, and the depth D may be measured using the measuring unit 564 of the second measurement instrument 520. The second measurement instrument 520 may be, for example, an optical scatterometry instrument.

The memory device 554 of the computer system 550 may store the first measurement data of the recess region 110, which are obtained using the first and second measurement instruments 510 and 520. The first measurement data may be stored in the memory device 554 through the interface unit 558 of the computer system 550. Further, commands for controlling the controller 552 may be stored in the memory device 554.

Referring to FIG. 4, a conductive pattern 120 may be formed to fill a portion of the recess region 110. The recess region 110 may include a lower region 110L adjacent to the bottom surface of the recess region 110 and an upper region 110U separated from the bottom surface of the recess region 110. In example embodiments, the conductive pattern 120 may be formed to fill the lower region 110L. The conductive pattern 120 may include, for example, a metal material.

The formation of the conductive pattern 120 may include forming a conductive layer on the semiconductor substrate 100 to fill the recess region 110 and etching the conductive layer to leave a portion of the conductive layer in the recess region 110 to a desired thickness. The conductive layer may be, for example, a metal layer. The forming of the conductive layer may be formed using, for example, a chemical vapor deposition process. The etching of the conductive layer may be performed using, for example, an etch-back process. The etching process may be performed to expose the top surface of the semiconductor substrate 100 and the side surfaces of the semiconductor substrate 100 defining the upper region 110U of the recess region 110.

Referring to FIGS. 1, 2A, and 4, second measurement data of the conductive pattern 120 may be obtained (in S20). The obtaining of the second measurement data may include measuring mass of an element contained in the conductive pattern 120. The mass of the element contained in the conductive pattern 120 may be obtained using the third measurement instrument 530 of the semiconductor measurement system 500. For example, the semiconductor substrate 100 provided with the conductive pattern 120 may be loaded on the chuck 562 of the third measurement instrument 530, and the mass of the element contained in the conductive pattern 120 may be measured by the measuring unit 564 of the third measurement instrument 530. The third measurement instrument 530 may be, for example, an X-ray fluorescence analysis instrument.

The mass of the element in the conductive pattern 120 obtained by the third measurement instrument 530 may be stored in the memory device 554 through the interface unit 558 of the computer system 550.

Referring to FIGS. 1, 2A, 4, and 6, a first volume V1 of the recess region 110 may be calculated from the first measurement data (in S30), a second volume V2 of the conductive pattern 120 may be calculated from the second measurement data (in S40), and a measurement target parameter R may be calculated from a difference between the first volume V1 and the second volume V2 (in S50). According to the present embodiment, the measurement target parameter R may be a distance between a top surface of the conductive pattern 120 and the top surface of the semiconductor substrate 100.

The calculation of the measurement target parameter R may be performed using a calculation module included in the calculator 552a of the computer system 550. Hereinafter, the calculation module may be described with reference to FIG. 6.

First, the first volume V1 of the recess region 110 may be calculated from the first measurement data. For example, the first volume V1 may be calculated using the following equation 1.

$$V1 = a \cdot A(m \cdot B + n),$$ [Equation 1]

where a, m, and n are constants. A is a measurement value of the width W of the recess region 110 obtained by the first measurement instrument 510, and B is a measurement value of the depth D of the recess region 110 obtained by the second measurement instrument 520. In the present specification, the measurement values may be obtained by a non-destructive testing method.

The first volume V1 of the recess region 110 may be obtained by multiplying an area of a virtual top surface U of the recess region 110 by the depth D.

Since the area of the virtual top surface U of the recess region 110 is proportional to the width W, it may be given by multiplying the measurement value A of the width W by a proportional factor a that is a constant. That is, the area of the virtual top surface U may be given by Aa.

The measurement value B of the depth D may be different from an actual value B' of the depth D. In the present specification, the actual value may be a value that is obtained using a destructive testing method. Accordingly, the calculation module may be performed in such a way that the measurement value B of the depth D is adjusted to become approximately the same as the actual value B' of the depth D.

For example, the forming of the recess region 110 in the semiconductor substrate 100 may include performing an anisotropic etching process, and each of the side surfaces of the recess region 110 may be formed to have a slanted profile, according to a process condition or property of the anisotropic etching process. Due to the slanted profile of the side surface, the measurement value B of the depth D obtained by the second measurement instrument 520 may be different from the actual value B' of the depth D.

Figure 7:
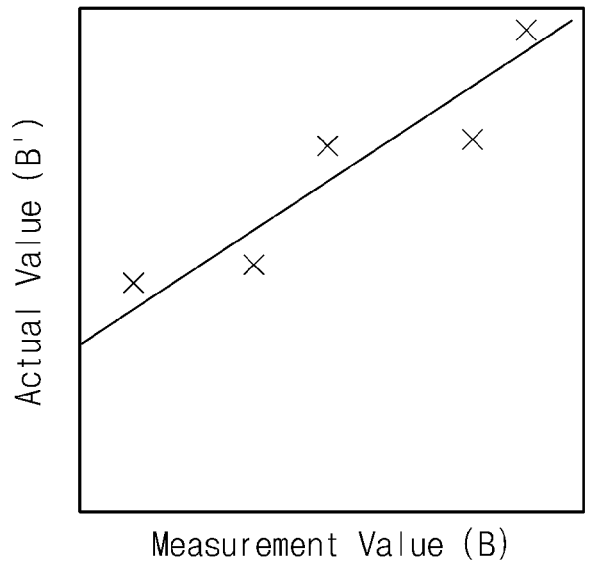
FIG. 7 is a graph showing a relationship between measured and actual values of a depth of a recess region.

FIG. 7 is a graph showing a relationship between measured and actual values of a depth of a recess region. The following experimental example shows that there is a correlation between the measurement value B of the depth D and the actual value B' of the depth D.

EXPERIMENTAL EXAMPLE

Samples may be provided. Each of the samples may be the semiconductor substrate 100 with the recess region 110, as described with reference to FIG. 3.

First, the measurement value B of the depth D of the recess region 110 of each of the samples may be obtained using the optical scatterometry instrument allowing the non-destructive testing method. Thereafter, an actual value B' of the depth D of the recess region 110 of each of the samples may be obtained using a scanning electron microscope (SEM) instrument or a transmission electron microscope (TEM) instrument, which may be used in the destructive testing method. FIG. 7 shows the correlation between the measurement and actual values B and B' of the depth D obtained from each of the samples.

Referring to FIG. 7, the actual value B' of the depth D is a function of the measurement value B of the depth D, and the correlation between the measurement and actual values B and B' of the depth D is given by the following equation 2.

$$B' = m \cdot B + n, \quad \text{[Equation 2]}$$

where m and n are constants that are determined through this empirical study.

According to the equation 2, the first volume V1 of the recess region 110 may be obtained by adjusting the measurement value B of the depth D in such a way that it becomes approximately the same as the actual value B' of the depth D. In other words, the first volume V1 may be calculated using the equation 1.

Next, the second volume V2 of the conductive pattern 120 may be calculated from the second measurement data. The second volume V2 may be calculated using the following equation 3.

$$V2 = c \cdot C, \quad \text{[Equation 3]}$$

where c is a constant. C is mass of an element in the conductive pattern 120 measured by the third measurement instrument 530. Since the volume of the conductive pattern 120 is proportional to the mass of the element contained in the conductive pattern 120, the second volume V2 may be given by multiplying the mass C of the element contained in the conductive pattern 120 by the constant c. The constant c may also be determined through empirical study.

Next, the measurement target parameter R may be calculated using a difference between the first volume V1 and the second volume V2. The measurement target parameter R may be calculated using the following equation 4.

$$R = \{aA(mB + n) - cC\}/aA \quad \text{[Equation 4]}$$
$$= mB - k(C/A) + n, \, (k = c/a),$$

where a, m, n, and c are the above described constants. A is a measurement value of the width W of the recess region 110 measured by the first measuring instrument 510, B is a measurement value of the depth D of the recess region 110 measured by the second measuring instrument 520, and C is the mass of the element in the conductive pattern 120 measured by the third measuring instrument 530.

Referring back to FIG. 6, the measurement target parameter R may be calculated by dividing a third volume V3, which is obtained by subtracting the second volume V2 of the conductive pattern 120 from the first volume V1 of the recess region 110, by the area (i.e., aA) of the virtual top surface U of the recess region 110.

The first volume V1 of the recess region 110 may be calculated by the equation 1, and the second volume V2 of the conductive pattern 120 may be calculated by the equation 3. Accordingly, the calculation module for calculating the measurement target parameter R may be performed using the equation 4.

Referring to FIGS. 1, 2A, and 2B, the calculation module for calculating the measurement target parameter R may be verified (in S60). The verifying of the calculation data of the calculation module may include obtaining reference data R' (in S61) and correcting the calculation data to reduce or minimize an error between the measurement target parameter R calculated by the calculation module and the reference data R' (in S63).

The reference data R' may be an actual value of the measurement target parameter R. For example, the reference data R' may be obtained using a scanning electron microscope (SEM) instrument or a transmission electron microscope (TEM) instrument, which may be used in the destructive testing method.

The correcting of the calculation module may include operating a verification module contained in the calculator 552a of the computer system 550. The operation of the verification module may be performed using the following equation 5.

$$MSE = \frac{1}{N} \sum_{K=1}^{N} \left\{ \left( mB_K - k\frac{C_k}{A_k} + n \right) - R'_K \right\}^2, \, (k = c/a) \quad \text{[Equation 5]}$$

where a, m, n, and c are the above described constants and N is an integer. The verification module may be operated using measurement values A, B, and C and reference data R' obtained from N samples. That is, $A_K$ is a measurement value of the width W of a K-th sample, $B_K$ is a measurement value of the depth D of the K-th sample, $C_K$ is mass of an element contained in the conductive pattern 120 of the K-th sample, and $R_K'$ is the reference data of the K-th sample.

By the verification module, the constants m, n, and k may be obtained in such a way that an error (i.e., mean squared error) between the measurement target parameter R obtained by the calculation module and the reference data R' is minimized.

The calculation module may be corrected using the constants m, n, and k obtained by the verification module. In the case where the calculation module is corrected, the step (S50 of FIG. 2A) of calculating the measurement target parameter R may be performed again using the corrected calculation module. By using the corrected calculation module, it is possible to obtain an optimized measurement target parameter Ropt. For example, the optimized measurement target parameter Ropt may be obtained by fitting the measurement value A of the width W of the recess region 110, the measurement value B of the depth D of the recess region 110, and the mass C of the element contained in the conductive pattern 120 in the corrected calculation module.

According to example embodiments of the inventive concepts, a measurement result can be precisely obtained by a method of directly measuring parameters of semiconductor patterns formed on a cell array region of a semiconductor substrate without using test patterns for measuring a three-dimensional semiconductor structure. In addition, since measurement target parameters are calculated using the measured parameters and a simple geometrical model, it is possible to reduce the time taken for the measurement. Accordingly, it is possible to improve reliability of the measurement and provide a method and/or a system capable of easily measuring a semiconductor device.

Figure 8:
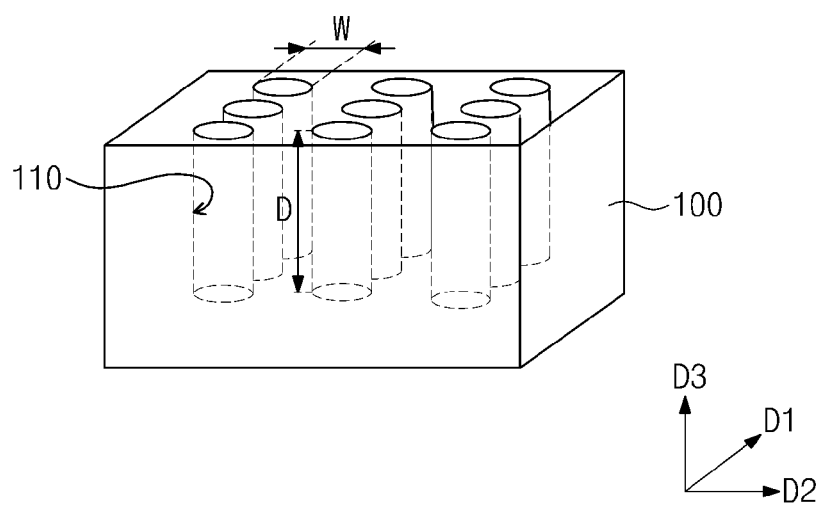
FIG. 8 and FIG. 9 are perspective views illustrating a method of measuring a semiconductor device according to another example embodiment of the inventive concepts.
Figure 9:
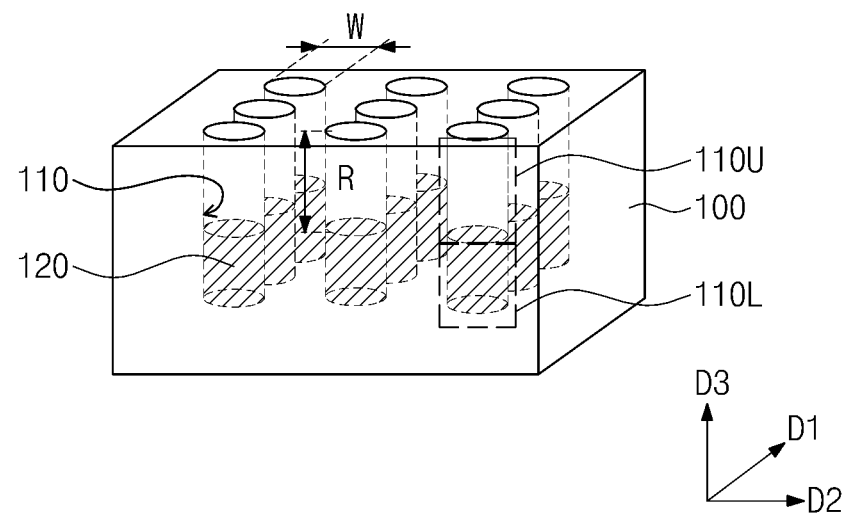
Figure 10:
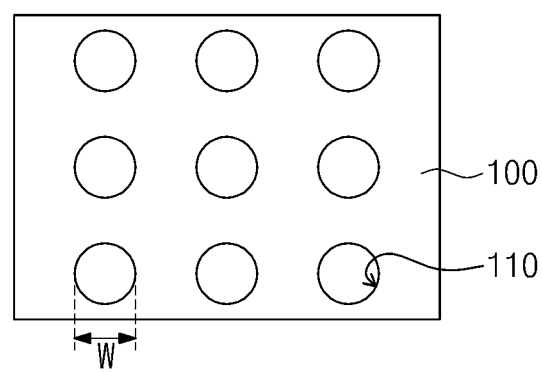
FIG. 10 is a plan view of FIG. 8.
Figure 11:
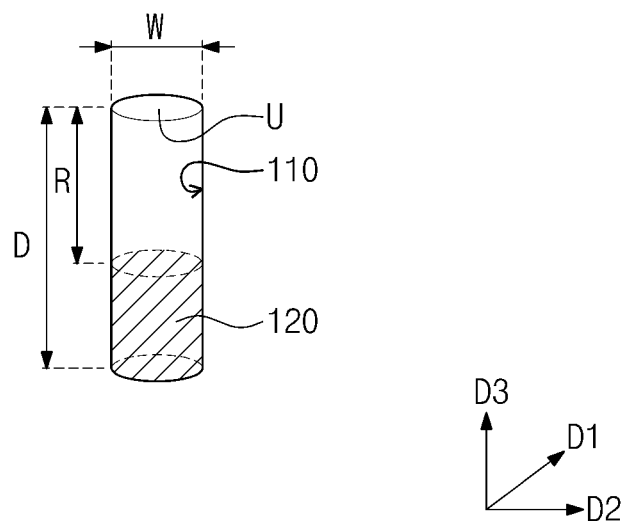
FIG. 11 is a geometrical model illustrating calculation parameters, which are used in a measurement method of a semiconductor device according to the example embodiment of the inventive concepts.

FIGS. 8 and 9 are perspective views illustrating a method of measuring a semiconductor device according to another example embodiment of the inventive concepts, and FIG. 10 is a plan view of FIG. 8. FIG. 11 is a geometrical model illustrating calculation parameters, which are used in a measurement method of a semiconductor device according to another example embodiment of the inventive concepts. For concise description, a previously described element may be identified by a similar or identical reference number without repeating an overlapping description thereof.

Referring to FIGS. 8 and 10, a plurality of recess regions 110 may be formed in a semiconductor substrate 100. Although not illustrated, the semiconductor substrate 100 may include a plurality of transistors and/or a plurality of conductive lines. According to the present embodiment, the recess region 110 may be formed to penetrate at least a portion of the semiconductor substrate 100 and may be shaped like a hole. The plurality of recess regions 110 may be spaced apart from each other in a first direction D1 and may be arranged along the first direction D1 to form a column. In addition, the plurality of recess regions 110 may be spaced apart from each other in a second direction D2 crossing the first direction D1 and may be arranged along the second direction D2 to form a row. In other words, the plurality of recess regions 110 may be two-dimensionally arranged on the semiconductor substrate 100.

Referring to FIGS. 1, 2A, 8, and 10, first measurement data of the recess region 110 may be obtained (in S10). The obtaining of the first measurement data may include measuring a width W of the recess region 110 and measuring a depth D of the recess region 110. In the present embodiment, the width W of the recess region 110 may be a diameter of the recess region 110 delimited by a side surface of the semiconductor substrate 100. In addition, the depth D of the recess region 110 may be defined as a distance between a top surface of the semiconductor substrate 100 and a bottom surface of the recess region 110.

The width W of the recess region 110 may be measured using the first measurement instrument 510 of the semiconductor measurement system 500. The first measuring instrument 510 may be, for example, a scanning electron microscope (SEM) instrument. The depth D of the recess region 110 may be measured using the second measurement instrument 520 of the semiconductor measurement system 500. The second measuring instrument 520 may be, for example, an optical scatterometry instrument.

The first measurement data of the recess region 110, which are obtained using the first and second measurement instruments 510 and 520, may be stored in the memory device 554 of the computer system 550 through the interface unit 558.

Referring to FIG. 9, a conductive pattern 120 may be formed to fill a portion of the recess region 110. The recess region 110 may include a lower region 110L adjacent to the bottom surface of the recess region 110 and an upper region 110U separated from the bottom surface of the recess region 110. In example embodiments, the conductive pattern 120 may be formed to fill the lower region 110L.

Referring to FIGS. 1, 2A, and 9, second measurement data of the conductive pattern 120 may be obtained (in S20). The obtaining of the second measurement data may include measuring mass of an element contained in the conductive pattern 120. The mass of the element contained in the conductive pattern 120 may be obtained using the third measurement instrument 530 of the semiconductor measurement system 500. The third measurement instrument 530 may be, for example, an X-ray fluorescence analysis instrument.

The mass of the element in the conductive pattern 120 obtained by the third measurement instrument 530 may be stored in the memory device 554 through the interface unit 558 of the computer system 550.

Referring to FIGS. 1, 2A, 9, and 11, a first volume V1 of the recess region 110 may be calculated from the first measurement data (in S30), a second volume V2 of the conductive pattern 120 may be calculated from the second measurement data (in S40), and a measurement target parameter R may be calculated from a difference between the first volume V1 and the second volume V2 (in S50). According to the present embodiment, the measurement target parameter R may be a distance between a top surface of the conductive pattern 120 and the top surface of the semiconductor substrate 100.

The calculation of the measurement target parameter R may be performed using a calculation module included in the calculator 552a of the computer system 550. Hereinafter, the calculation module may be described with reference to FIG. 11.

First, the first volume V of the recess region 110 may be calculated from the first measurement data. The first volume V1 may be calculated using the equation 1.

The first volume V1 of the recess region 110 may be obtained by multiplying an area of a virtual top surface U of the recess region 110 by the depth D. As will be understood, the area calculation (e.g., a circle) of the top surface in this embodiment differs from the previous embodiment (e.g., a rectangle).

Since the area of the virtual top surface U of the recess region 110 is proportional to the width W, it may be given by multiplying the measurement value A of the width W by a proportional factor a that is a constant. That is, the area of the virtual top surface U may be given by Aa.

The measurement value B of the depth D may be different from an actual value B' of the depth D. Accordingly, the calculation module may be performed in such a way that the measurement value B of the depth D is adjusted to become approximately the same as the actual value B' of the depth D.

For example, the forming of the recess region 110 in the semiconductor substrate 100 may include performing an anisotropic etching process, and each of the side surfaces of the recess region 110 may be formed to have a slanted profile, according to a process condition or property of the anisotropic etching process. Due to the slanted profile of the side surface, the measurement value B of the depth D obtained by the second measurement instrument 520 may be different from the actual value B' of the depth D.

Referring back to FIG. 7, the correlation between the measurement and actual values B and B' of the depth D is given by the equation 2. According to the equation 2, the measurement value B of the depth D may be corrected to be approximately the same as the actual value B' of the depth D. Accordingly, the first volume V1 of the recess region 110 can be obtained by the equation 1.

Next, the second volume V2 of the conductive pattern 120 may be calculated from the second measurement data. The second volume V2 may be calculated by the equation 3. Since the second volume V2 of the conductive pattern 120 is proportional to the mass C of the element contained in the conductive pattern 120, the second volume V2 may be obtained by multiplying the mass C of the element contained in the conductive pattern 120 by the constant c.

Next, the measurement target parameter R of the recess region 110 may be calculated using a difference between the first volume V1 and the second volume V2. The measurement target parameter R may be calculated by the equation 4.

Referring back to FIG. 11, the measurement target parameter R may be calculated by dividing a third volume V3, which is obtained by subtracting the second volume V2 of the conductive pattern 120 from the first volume V1 of the recess region 110, by the area (i.e., aA) of the virtual top surface U of the recess region 110.

The first volume V1 of the recess region 110 may be calculated by the equation 1, and the second volume V2 of the conductive pattern 120 may be calculated by the equation 3. Accordingly, the calculation module for calculating the measurement target parameter R may be performed using the equation 4.

The calculation module, which is used to calculate the measurement target parameter R may be verified in the same manner as the measurement method described with reference to FIGS. 1, 2A, and 2B.

Figure 12:
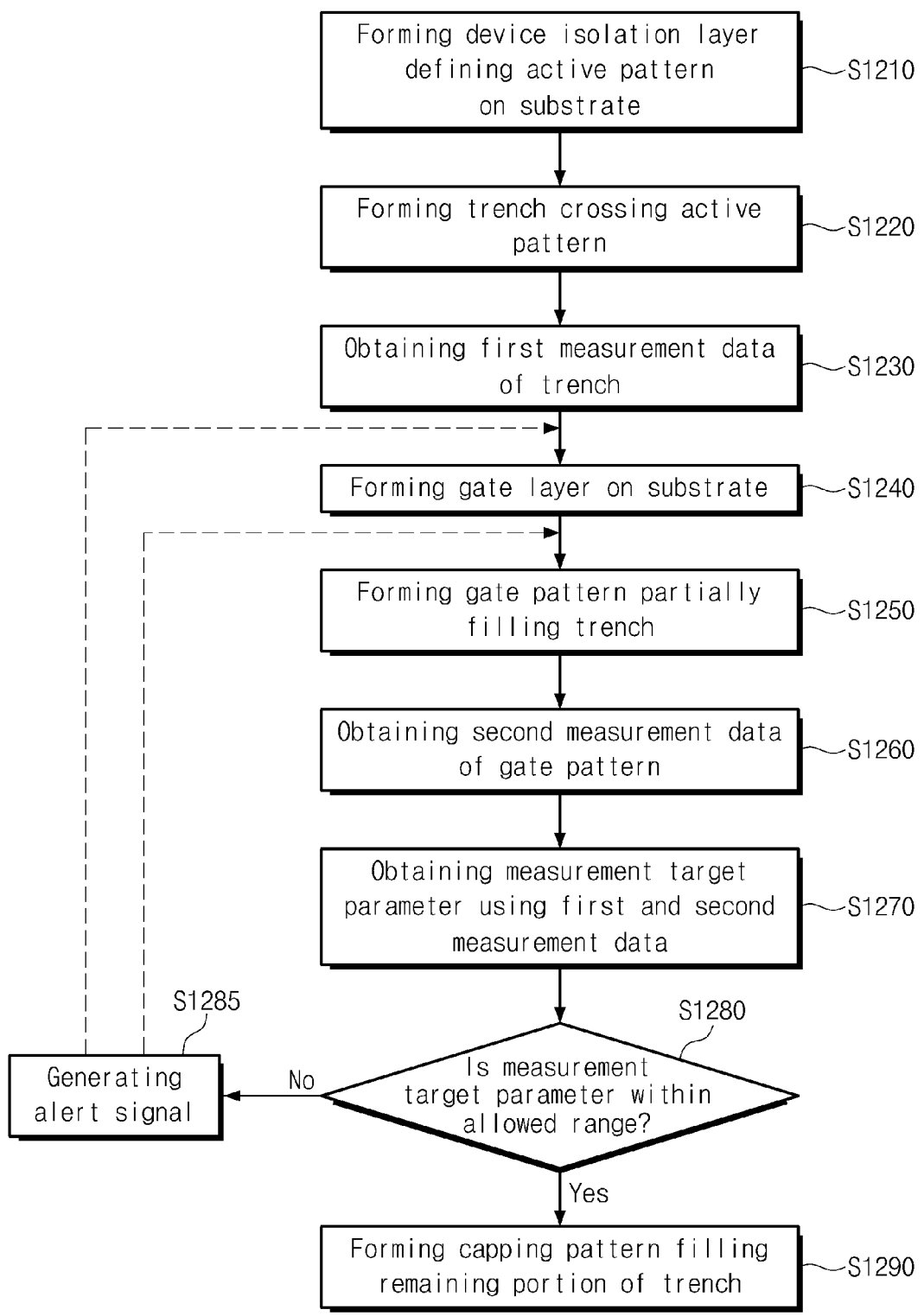
FIG. 12 is a flow chart illustrating a method of fabricating a semiconductor device according to a further example embodiment of the inventive concepts.

FIG. 12 is a flow chart illustrating a method of fabricating a semiconductor device according to a further embodiment of the inventive concepts. FIGS. 13A through 17A are plan views illustrating a method of fabricating a semiconductor device according to the further example embodiment of the inventive concepts, and FIGS. 13B through 17B are sectional views taken along line I-I' of FIGS. 13A through 17A, respectively.

Figure 13A:
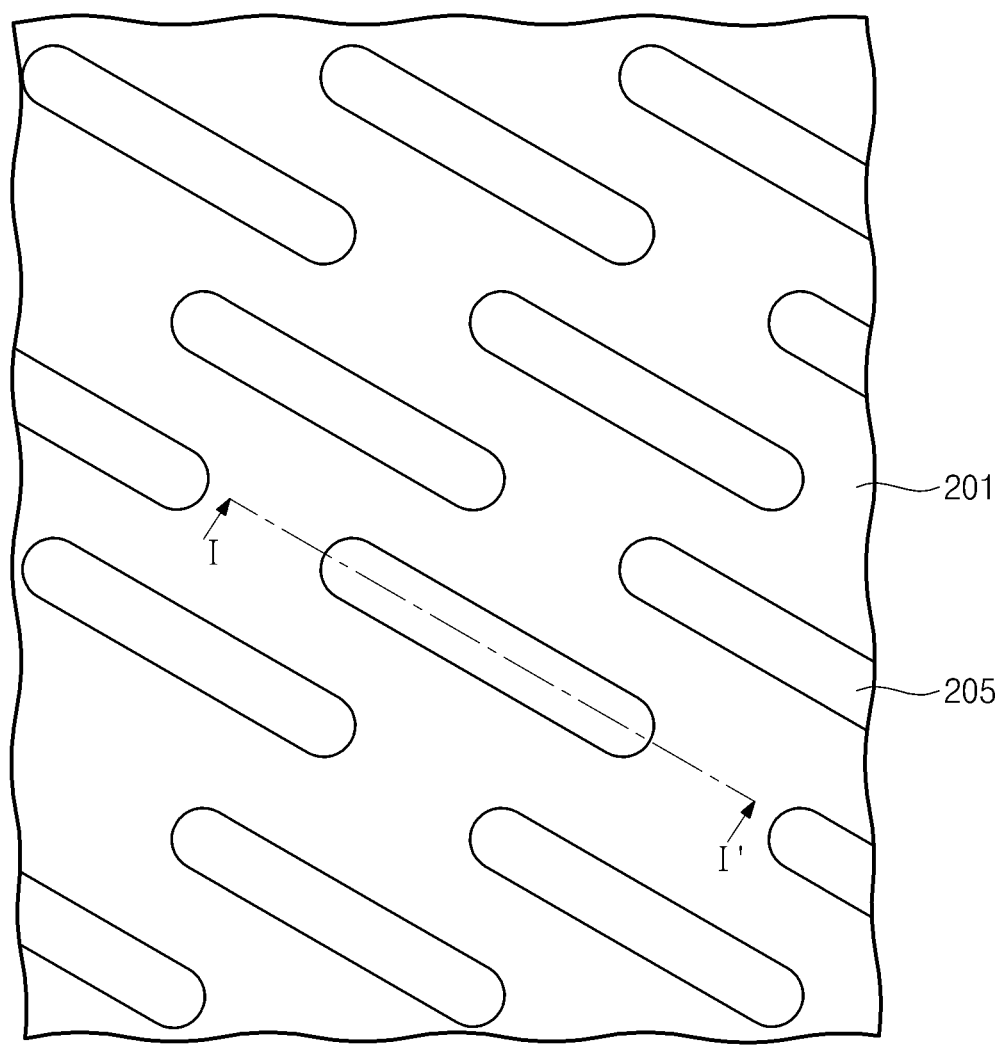
Figure 13B:
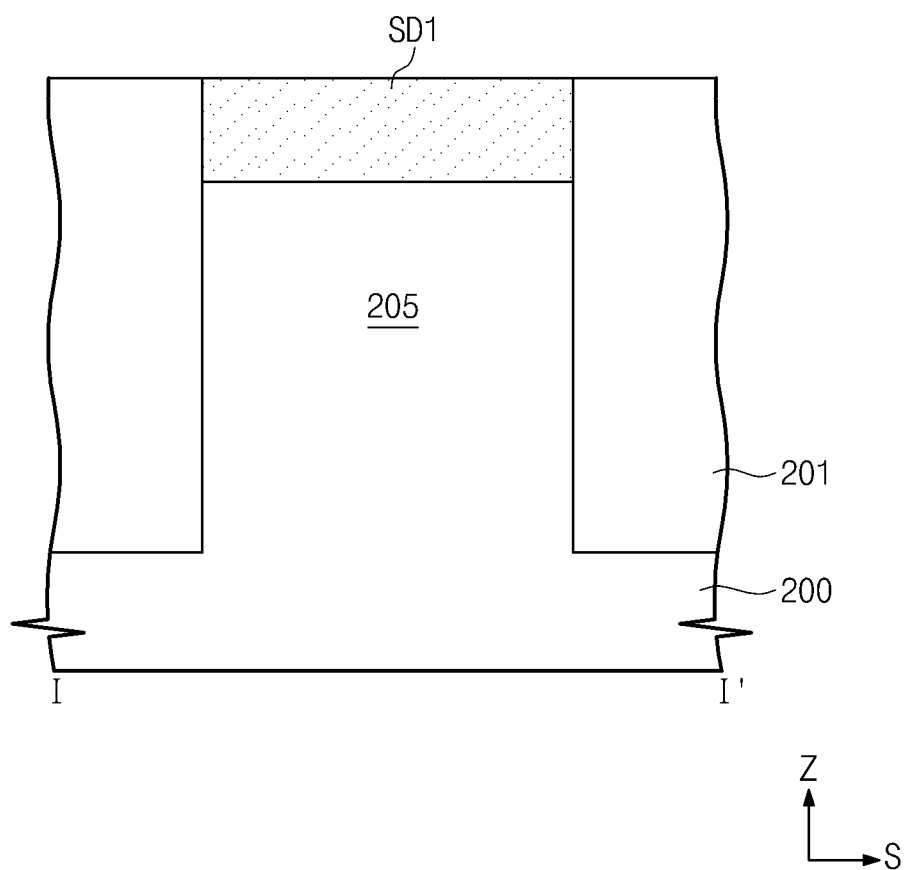

Referring to FIGS. 12, 13A, and 13B, a device isolation layer 201 may be formed on a substrate 200 to define active patterns 205 (in S1210). The substrate 200 may be a semiconductor wafer such as a silicon wafer, a germanium wafer, or a silicon-germanium wafer. In example embodiments, when viewed in a plan view, the active pattern 205 may have a bar shape and may be disposed in such a way that its longitudinal axis is parallel to a third direction (e.g., S direction) crossing both of the first and second directions (e.g., X and Y directions), which cross each other. FIG. 13B is a sectional view taken along a plane containing third and fourth directions S and Z, where the fourth direction Z is perpendicular to all of the first, second, and third directions X, Y, and S. The device isolation layer 201 may be formed using, for example, a shallow trench isolation (STI) technology. The device isolation layer 201 may include at least one of a silicon nitride layer, a silicon oxide layer, and/or a silicon oxynitride layer.

A first impurity injection region SD1 may be formed in an upper portion of the active pattern 205. The first impurity injection region SD1 may be formed using an ion implantation process. For example, the first impurity injection region SD1 may be a doped region, in which n-type dopants are injected.

Figure 14A:
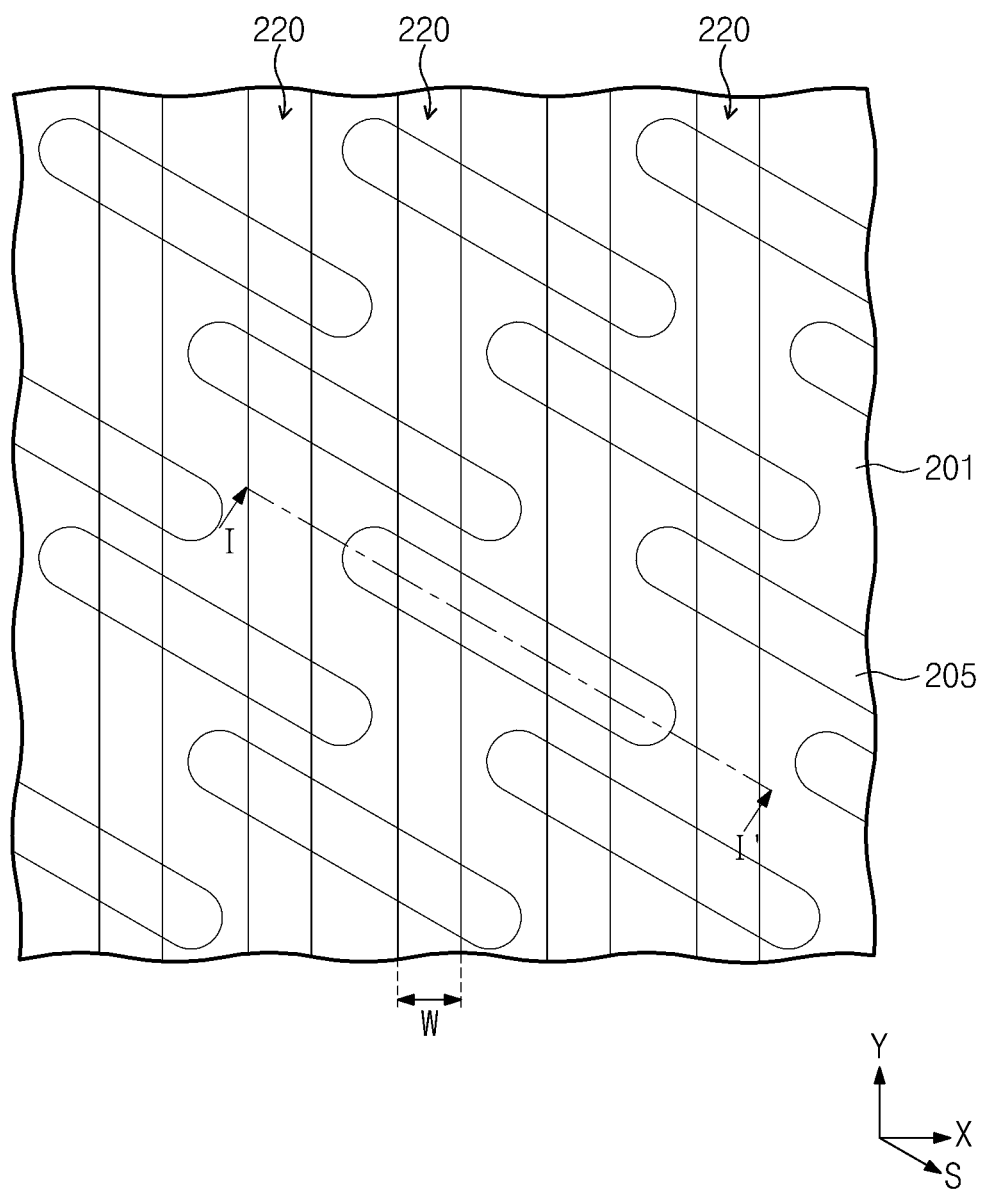

Referring to FIGS. 12, 14A, and 14B, a plurality of trenches 220 may be formed in the substrate 200 to cross the active patterns 205 (in S1220). The formation of the trenches 220 may include forming mask patterns on the substrate 200 to define regions for the trench 220 and then etching the substrate 200 and the device isolation layer 201 using the mask patterns as an etch mask. The mask patterns may be a hard mask pattern (e.g., made of a silicon nitride layer) or a photoresist pattern. The etching step may be performed in such a way that each of the trenches 220 can have a line-shaped structure extending along the second direction Y. The trenches 220 may be formed to be spaced apart from each other in the first direction X. Thereafter, the mask patterns may be removed. In the case where the mask patterns are the photoresist patterns, the mask patterns may be removed by an ashing process. In the case where the mask patterns are the hard mask patterns (e.g., the silicon nitride layer), the mask patterns may be removed by a cleaning process using phosphoric acid and so forth.

First measurement data of the trenches 220 may be obtained (in S1230). The obtaining of the first measurement data may include measuring a width W of the trench 220 and measuring a depth D of the trench 220. The obtaining of the first measurement data may be performed in the same manner as the step S10 of FIG. 2A.

For example, the width W of the trench 220 may be measured by the first measurement instrument 510 of the semiconductor measurement system 500 described with reference to FIG. 1. The first measurement instrument 510 may be, for example, a scanning electron microscope (SEM) instrument. The depth D of the trench 220 may be measured by the second measurement instrument 520 of the semiconductor measurement system 500. The second measurement instrument 520 may be, for example, an optical scatterometry instrument. The first measurement data may be stored in the memory device 554 through the interface unit 558 of the computer system 550.

Figure 15A:
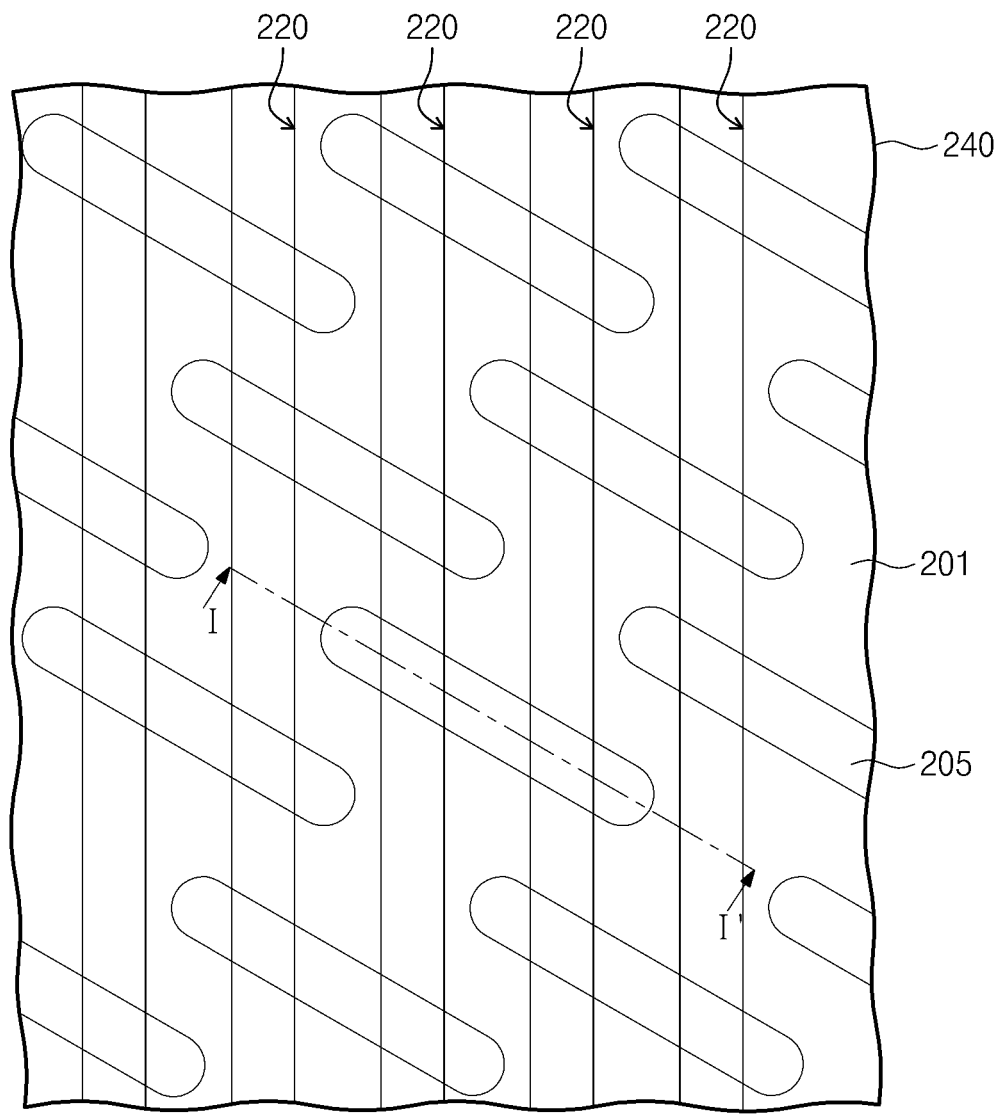
Figure 15B:
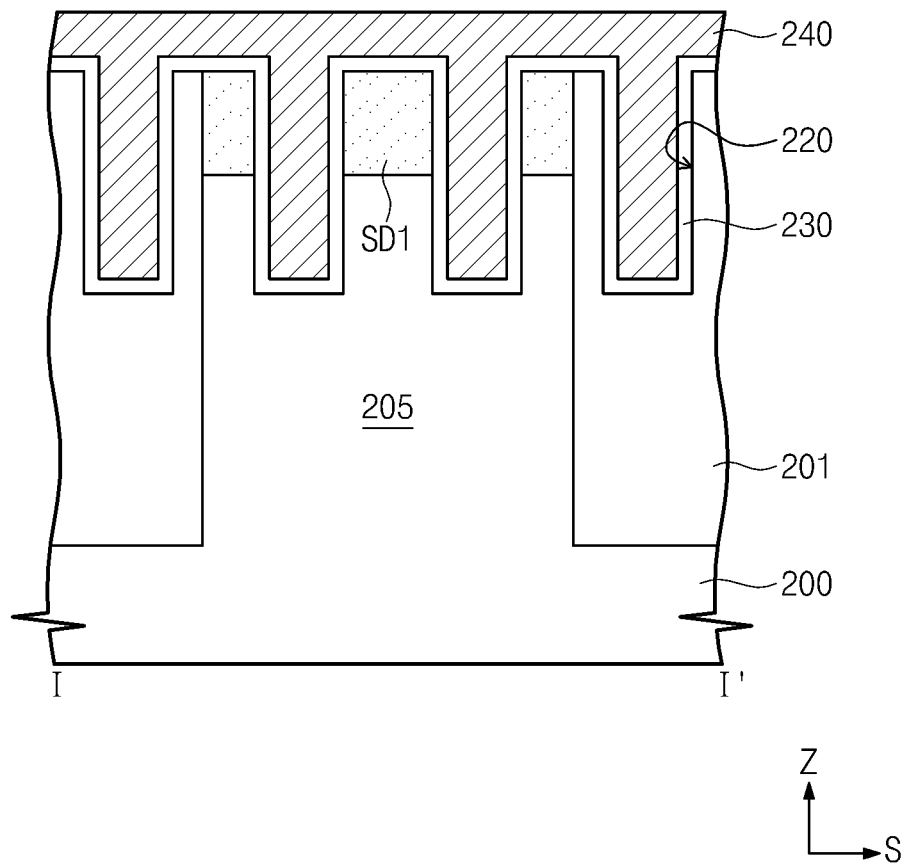

Referring to FIGS. 12, 15A, and 15B, a gate insulating layer 230 may be formed on the substrate 200. The gate insulating layer 230 may be formed to fill a portion of the trench 220. The gate insulating layer 230 may be formed to cover bottom and side surfaces of the trench 220. The gate insulating layer 230 may be formed using a thermal oxidation process, an atomic layer deposition, a chemical vapor deposition process, and so forth. For example, the gate insulating layer 230 may include a silicon oxide layer.

Next, a gate layer 240 may be formed on the substrate 200 (in S1240). The gate layer 240 may be formed to fill the remaining portion of the trench 220. The gate insulating layer 230 may be interposed between the substrate 200 and the gate layer 240 and between the device isolation layer 201 and the gate layer 240. The gate layer 240 may be formed using a chemical vapor deposition process and so forth. The gate layer 240 may include one of conductive materials including doped semiconductor materials (e.g., doped silicon or doped germanium), conductive metal nitrides (e.g., titanium nitride or tantalum nitride), metals (tungsten, titanium, or tantalum), or metal-semiconductor compounds (tungsten silicide, cobalt silicide, or titanium silicide).

Figure 16A:
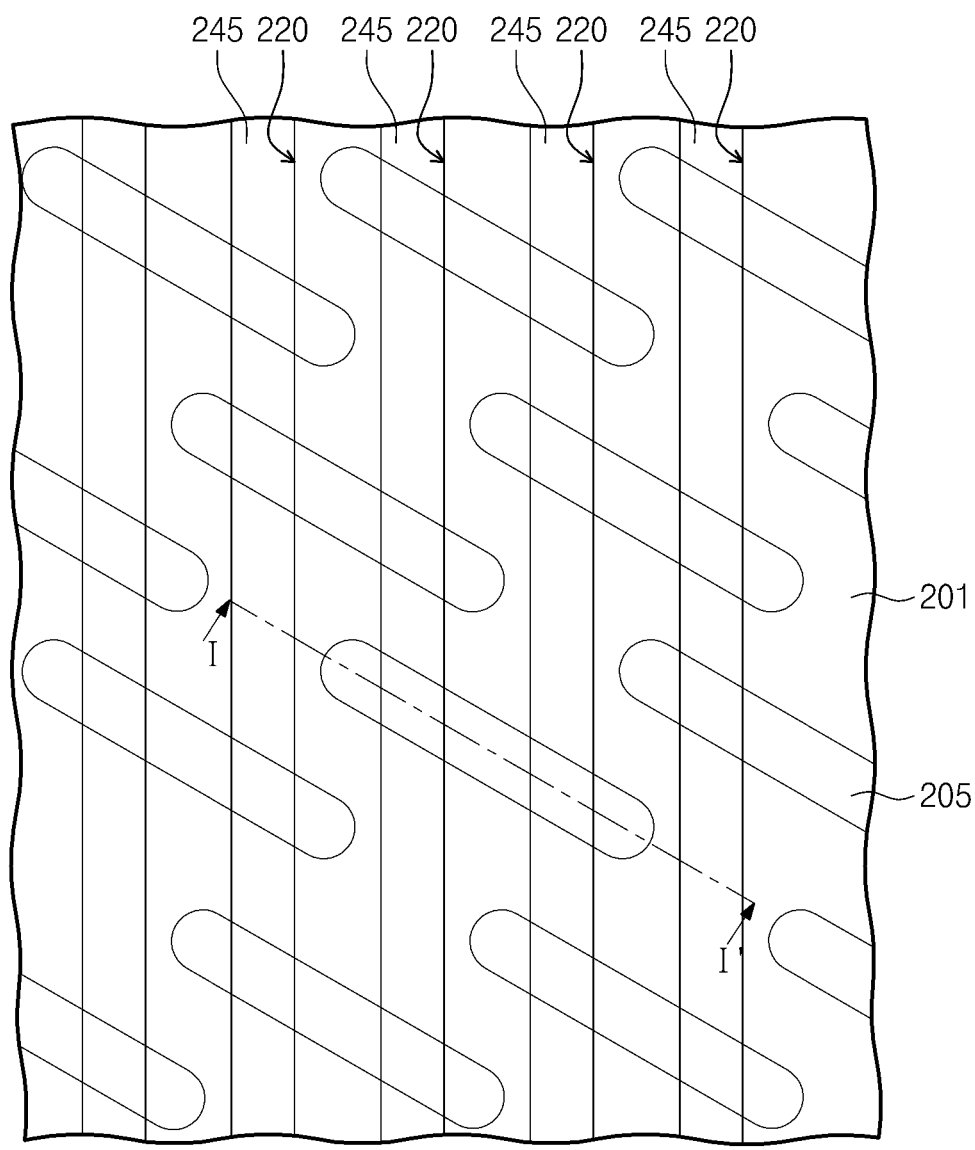
Figure 16B:
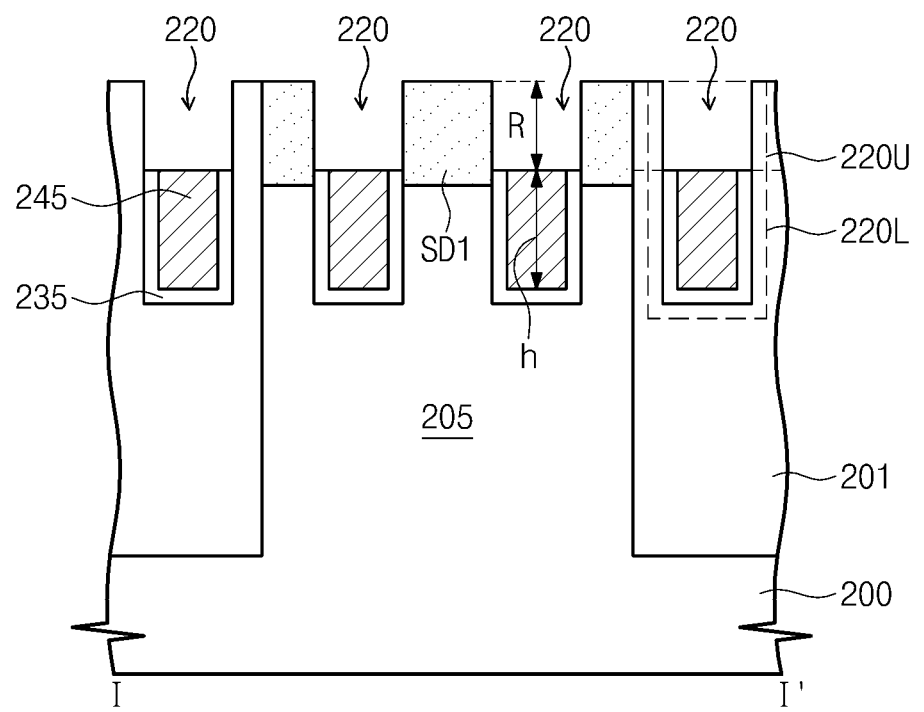

Referring to FIGS. 12, 16A, and 16B, the gate layer 240 may be etched to form a gate pattern 245 filling a portion of the trench 220 (in S1250). The formation of the gate pattern 245 may include etching the gate layer 240 in such a way that a portion of the gate layer 240 remaining in the trench 220 has a desired thickness. For example, the etching process may be performed using an etch-back process. The trench 220 may include a lower region 220L adjacent to a bottom surface of the trench 220 and an upper region 220U apart from the bottom surface of the trench 220. As the result of the etching process, the gate pattern 245 may be formed to fill the lower region 220L of the trench 220.

Next, the gate insulating layer 230 may be etched to form a gate insulating pattern 235 in the trench 220. The gate insulating pattern 235 may be interposed between the substrate 200 and the gate pattern 245 and between the device isolation layer 201 and the gate pattern 245. The gate insulating pattern 235 may be formed to have a top surface that is substantially coplanar with a top surface of the gate pattern 245. The formation of the gate insulating pattern 235 may be performed to expose top surfaces of the substrate 200 and the device isolation layer 201 and side surfaces of the upper region 220U of the trench 220.

Second measurement data of the gate pattern 245 may be obtained (in S1260). The obtaining of the second measurement data may include measuring mass of an element contained in the gate pattern 245. The obtaining of the second measurement data may be performed in the same manner as the step S20 of FIG. 2A.

For example, the mass of the element contained in the gate pattern 245 may be obtained by the third measurement instrument 530 of the semiconductor measurement system 500 described with reference to FIG. 1. The third measurement instrument 530 may be, for example, an X-ray fluorescence analysis instrument.

The mass of the element in the conductive pattern 220 obtained by the third measurement instrument 530 may be stored in the memory device 554 through the interface unit 558 of the computer system 550.

A measurement target parameter R may be obtained using the first and second measurement data (in S1270). In the present embodiment, the measurement target parameter R may be a distance between top surfaces of the gate pattern 245 and the substrate 200. The obtaining of the measurement target parameter R may be performed in the same manner as those described with reference to the steps S30 to S60 of FIG. 2A and FIG. 2B.

For example, the obtaining of the measurement target parameter R may include calculating a first volume V1 of the trench 220 using the first measurement data (in S30 of FIG. 2A), calculating a second volume V2 of the gate pattern 245 using the second measurement data (in S40 of FIG. 2A), and calculating the measurement target parameter R using a difference between the first and second volumes V and V2 (in S50 of FIG. 2A). The calculation of the measurement target parameter R may be performed using the calculation module included in the calculator 552a of the computer system 550 described with reference to FIG. 1. The calculation module may be performed using the equations 1 to 4.

The first volume V1 of the trench 220 may be calculated using the equation 1. For example, the first volume V1 of the trench 220 may be calculated by substituting measurement values of the width W and depth D of the trench 220 in the variables A and B of the equation 1. The second volume V2 of the gate pattern 245 may be calculated using the equation 3. For example, in the equation 3, the variable C may be the mass of the element contained in the gate pattern 245. The measurement target parameter R may be calculated using the equation 4. As will be appreciated the top surface areas used will depend on the top surface areas of the structures in this embodiment.

The obtaining of the measurement target parameter R may further include verifying the calculation module for calculating the measurement target parameter R (in S60 of FIG. 2A). The verifying of the calculation module may include obtaining reference data R' (in S61 of FIG. 2B) and correcting the calculation module to reduce or minimize an error between the measurement target parameter R calculated by the calculation module and the reference data R' (in S63 of FIG. 2B).

The reference data R' may be an actual value of the measurement target parameter R. The reference data R' may be obtained using, for example, a scanning electron microscope (SEM) instrument or a transmission electron microscope (TEM) instrument, which may be used in the destructive testing method.

The correcting of the calculation module may include operating a verification module contained in the calculator 552a of the computer system 550, as described with reference to FIG. 1. The operation of the verification module may be performed using the equation 5.

By operating the verification module, the calculation module can be corrected to reduce or minimize an error between the measurement target parameter R calculated by the calculation module and the reference data R'. In the case where the calculation module is corrected, the step (S5O of FIG. 2A) of calculating the measurement target parameter R may be performed again using the corrected calculation module. By using the corrected calculation module, it is possible to obtain an optimized measurement target parameter Ropt. For example, the optimized measurement target parameter Ropt may be obtained by fitting the measurement value A of the width W of the trench 220, the measurement value B of the depth D of the trench 220, and the mass C of the element contained in the gate pattern 245 in the corrected calculation module.

Referring back to FIG. 12, a step of examining whether the measurement target parameter R obtained is within an allowed range may be performed (in S1280).

If the measurement target parameter R is outside the allowed range, an alert signal may be generated (in S1285). Thereafter, if the measurement target parameter R is smaller than a lower limit of the allowed range (i.e. the gate pattern 245 is insufficiently etched), the etching process for forming the gate pattern 245 (in S1250) may be performed again. The etching process may be performed using, for example, an etch-back process. If the measurement target parameter R is higher than an upper limit of the allowed range (i.e. the gate pattern 245 is over-etched), the step S1240 for forming the gate layer 240 may be restarted to perform the deposition and etching processes again. For example, the gate insulating layer 230 may be additionally deposited on the substrate 200 with the gate pattern 245 and may be etched to form the gate insulating pattern 235 again on both sidewalls of the trench 220, and the processes of depositing and etching the gate layer 240 may be performed again.

In general, a thickness h of the gate pattern 245 (i.e., a distance between bottom and top surfaces of the gate pattern 245) may affect characteristics of a transistor including the gate pattern 245. A step of monitoring the measurement target parameter R may be needed to monitor more easily the thickness h of the gate pattern 145.

By fabricating a semiconductor device using a method and/or a system of measuring a semiconductor device according to example embodiments of the inventive concepts, it is possible to monitor exactly and easily the measurement target parameter R during the fabrication process of the semiconductor device. Accordingly, it is possible to improve reliability of the semiconductor device. In other words, a semiconductor device can be fabricated to have improved reliability.

Figure 17A:
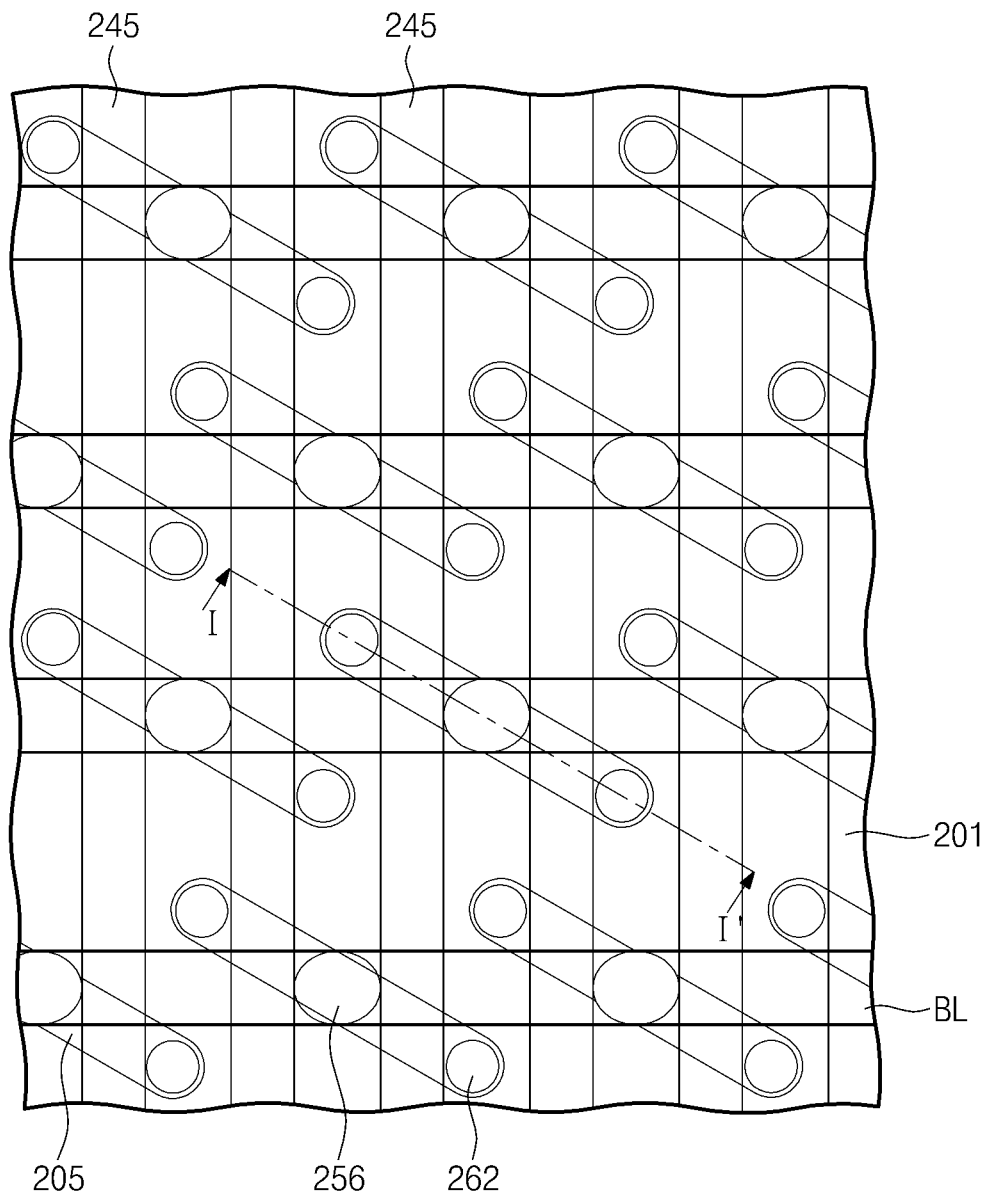
Figure 17B:
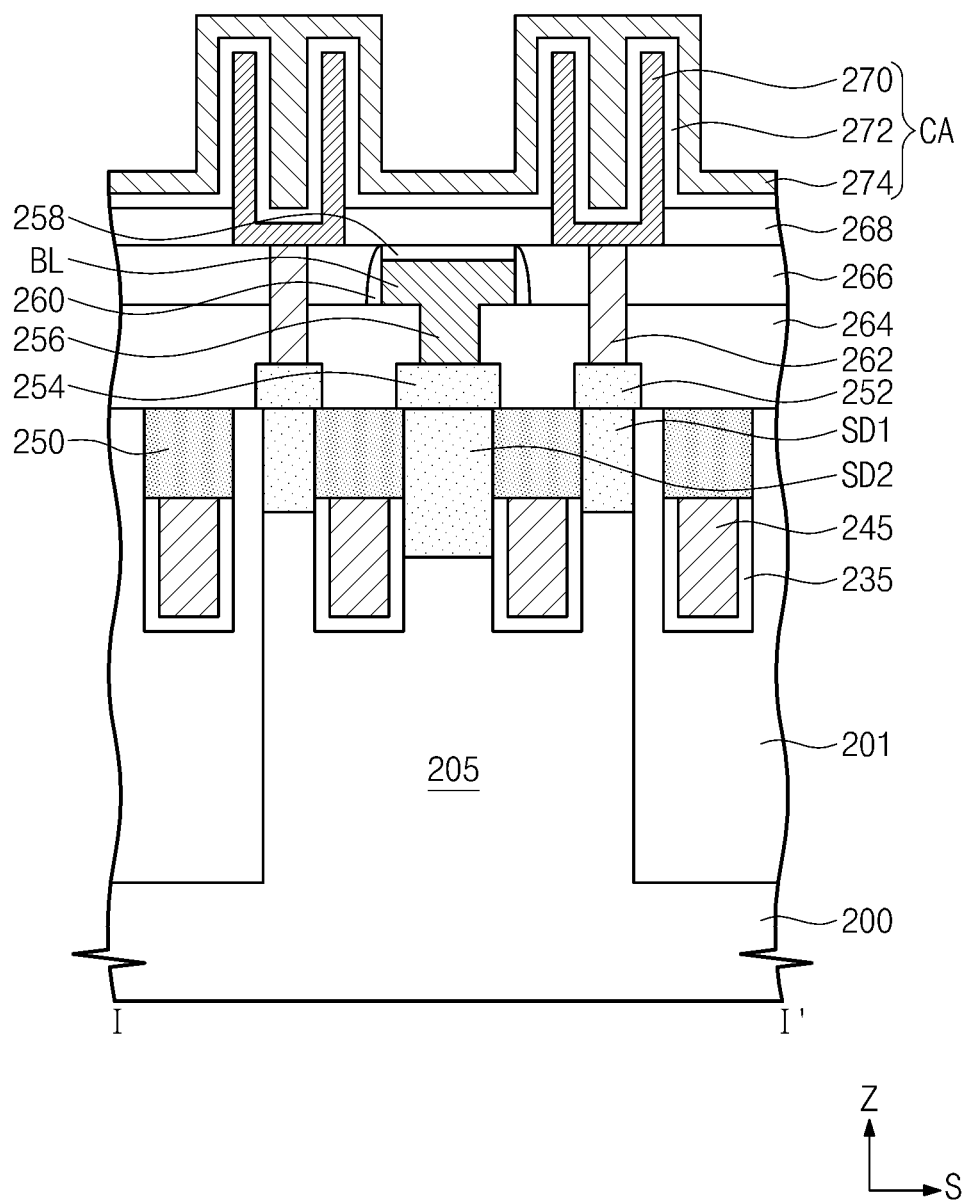

Referring to FIGS. 12, 17A, and 17B, if the measurement target parameter R is within the allowed range, a capping pattern 250 may be formed to fill the remaining portion of the trench 220 (in S1290). The formation of the capping pattern 250 may include forming a capping layer on the substrate 200 to fill the remaining portion of the trench 220 and planarizing the capping layer. The capping layer may include one of a silicon nitride layer, a silicon oxide layer, or a silicon oxynitride layer. The planarization process may be performed in such a way that a top surface of the capping pattern 250 becomes coplanar with that of the substrate 200.

An ion implantation process may be performed on the substrate 200 to form a second impurity injection region SD2 in the upper portion of the active pattern 205 and between an adjacent pair of the gate patterns 245. The second impurity injection region SD2 may be doped to have the same conductivity type as the first impurity injection region SD1 or contain n-type impurities. The second impurity injection region SD2 may be formed to have a bottom surface lower than that of the first impurity injection region SD1.

A doped poly-silicon layer, a doped single crystalline silicon layer, or a conductive layer may be formed on the substrate 200 and may be patterned to form a first pad 252 and a second pad 254. The first pad 252 may be connected to the first impurity injection region SD1, and the second pad 254 may be connected to the second impurity injection region SD2. If the first and second pads 252 and 254 include a poly-silicon or single crystalline silicon layer doped with impurities, the first and second pads 252 and 254 may be doped to have the same conductivity type as the first and second impurity injection regions SD1 and SD2.

A first interlayered insulating layer 264 may be formed on the first and second pads 252 and 254. The first interlayered insulating layer 264 may be formed using a chemical vapor deposition process. The first interlayered insulating layer 264 may include a silicon oxide layer, a silicon nitride layer, or a silicon oxynitride layer. A portion of the first interlayered insulating layer 264 may be patterned to form a contact hole, in which a direct contact will be formed. The contact hole may be formed to expose a top surface of the second pad 254. A conductive layer may be formed on the first interlayered insulating layer 264. The conductive layer may be formed to fill the contact holes. For example, the conductive layer may include a conductive material (e.g., metals or doped semiconductors). A mask layer may be formed on the conductive layer. For example, the mask layer may include one of a silicon nitride layer, a silicon oxide layer, or a silicon oxynitride layer. The mask layer and the conductive layer may be patterned to form a bit line BL and a mask pattern 258 disposed thereon. A direct contact 256 may be formed in the contact hole. The direct contact 256 may be connected to the second pad 254. An insulating spacer layer may be conformally deposited on the first interlayered insulating layer 264 and may be anisotropically etched to form insulating spacers 260 on sidewalls of the bit line BL. The insulating spacers 260 may include one of a silicon nitride layer, a silicon oxide layer, and a silicon oxynitride layer.

A second interlayered insulating layer 266 may be formed on the first interlayered insulating layer 264, and a planarization process may be performed to expose a top surface of the mask pattern 258. Thereafter, a buried contact 262 may be formed through the first and second interlayered insulating layers 264 and 266 and may be connected to the first pad 252. The buried contact 262 may include a conductive material (e.g., doped silicon and metals). A supporting layer 268 may be formed on the second interlayered insulating layer 266. The supporting layer 268 may include one of a silicon oxide layer, a silicon nitride layer, or a silicon oxynitride layer. The supporting layer 268 may be formed using, for example, a chemical vapor deposition process. A lower electrode 270 may be formed through the supporting layer 268 and may be connected to the buried contact 262. The lower electrode 270 may be formed to have a shape of a bottom-closed cylinder. A dielectric 272 may be formed to conformally cover the lower electrode 270, and an upper electrode 274 may be formed to cover the lower electrode 270 covered with the dielectric 272, thereby forming a capacitor CA. The lower electrode 270 and the upper electrode 274 may include a doped silicon layer, a metal layer, or a metal compound layer.

The semiconductor device fabrication process may be used using the measurement method exemplarily described with reference to FIGS. 3 through 6, but example embodiments of the inventive concepts may not be limited thereto. The measurement method described with reference to FIGS. 8 through 11 may be used for the semiconductor device fabrication process including a step of forming contact holes, which penetrate at least a portion of a semiconductor substrate and expose transistors and/or conductive lines provided on the semiconductor substrate, and a step of forming contact plugs, which fill partially the contact holes and are connected to the transistors and/or the conductive lines.

Figure 18:
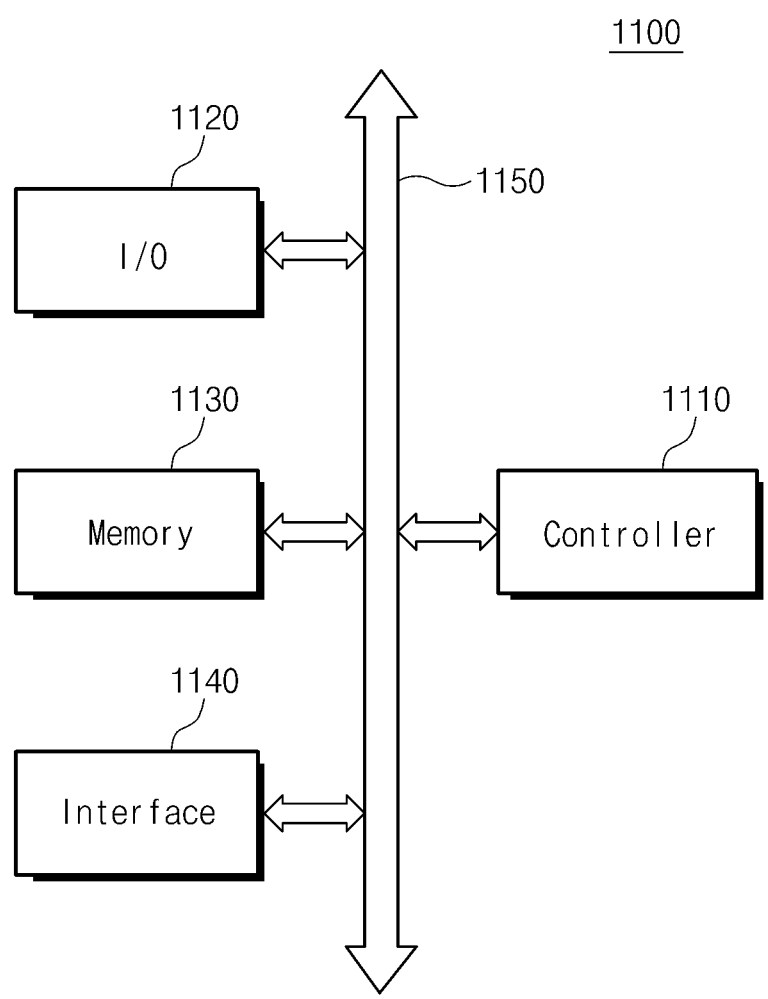
FIG. 18 is a schematic block diagram illustrating an example of electronic systems including a semiconductor device according to an example embodiment of the inventive concepts.

FIG. 18 is a block diagram illustrating an example of electronic systems including a semiconductor device according to example embodiments of the inventive concepts.

Referring to FIG. 18, an electronic system 1100 according to an example embodiment of the inventive concepts may include a controller 1110, an input/output (I/O) unit 1120, a memory device 1130, an interface unit 1140 and a data bus 1150. At least two of the controller 1110, the I/O unit 1120, the memory device 1130 and the interface unit 1140 may communicate with each other through the data bus 1150. The data bus 1150 may correspond to a path through which electrical signals are transmitted.

The controller 1110 may include a microprocessor, a digital signal processor, a microcontroller and/or another logic device. The other logic device may have a similar function to the microprocessor, the digital signal processor and/or the microcontroller. The I/O unit 1120 may include a keypad, a keyboard and/or a display unit. The memory device 1130 may store data and/or commands. The memory device 1130 may include at least one of the semiconductor devices according to the embodiments mentioned above. The memory device 1130 may further include another type of data storing devices, which are different from the data storing devices described above. The interface unit 1140 may transmit electrical data to a communication network and/or may receive electrical data from a communication network. The interface unit 1140 may operate by wireless and/or cable. For example, the interface unit 1140 may include an antenna for wireless communication and/or a transceiver for cable communication.

The electronic system 1100 may be applied to a laptop computer, a personal digital assistant (PDA), a portable computer, a web tablet, a wireless phone, a mobile phone, a digital music player, a memory card and/or other electronic products.

Figure 19:
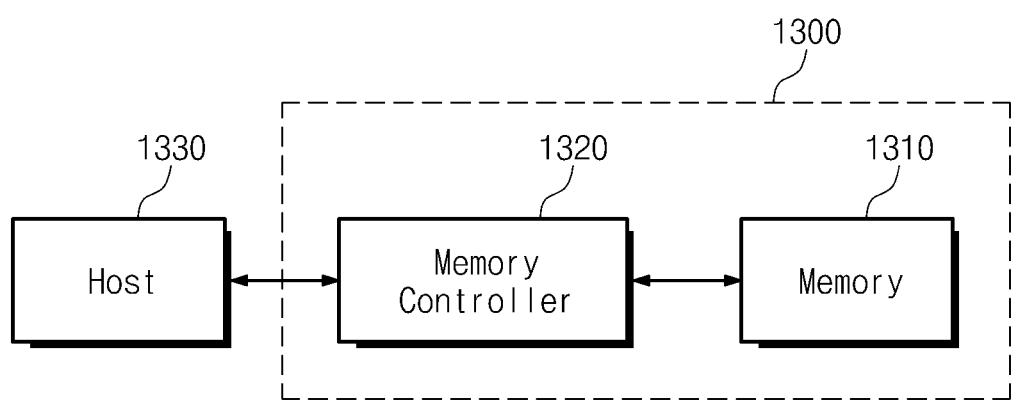
FIG. 19 is a schematic block diagram illustrating an example of memory cards including a semiconductor device according to an example embodiment of the inventive concepts.

FIG. 19 is a schematic block diagram illustrating an example of a memory card including a semiconductor device according to an example embodiment of the inventive concepts.

Referring to FIG. 19, a memory card 1300 according to an embodiment of the inventive concepts may include a memory device 1310. The memory device 1310 may include at least one of the semiconductor devices according to the embodiments mentioned above. In other embodiments, the memory device 1310 may further include other types of semiconductor devices, which are different from the semiconductor devices according to the embodiments described above. The memory card 1300 may include a memory controller 1320 that controls data communication between a host 1330 and the memory device 1310.

According to example embodiments of the inventive concepts, a measurement result can be precisely obtained by a method of directly measuring parameters of semiconductor patterns formed on a cell array region of a semiconductor substrate. In addition, since measurement target parameters are calculated using the measured parameters and a simple geometrical model, it is possible to reduce the time taken for the measurement. Accordingly, it is possible to improve reliability of the measurement and provide a method and a system capable of easily measuring a semiconductor device.

Further, since the measurement method and system according to example embodiments of the inventive concepts are used to fabricate a semiconductor device, it is possible to improve reliability of the semiconductor device. In other words, the semiconductor device can be fabricated to have improved reliability.

While example embodiments of the inventive concepts have been particularly shown and described, it will be understood by one of ordinary skill in the art that variations in form and detail may be made therein without departing from the spirit and scope of the attached claims.

What is claimed is:

1. A method of fabricating a semiconductor device, comprising: forming a device isolation layer on a substrate to define an active pattern, wherein the active pattern is a portion of the substrate that is penetrating through the device isolation layer;
   etching the substrate and the device isolation layer to form a trench crossing the active pattern, wherein the trench is formed in the substrate;
   obtaining a first measurement data from the trench using a scanning electron microscope and an optical scatterometry instrument, the scanning electron microscope including a first chuck and the optical scatterometry instrument including a second chuck, the obtaining the first measurement data including measuring a width of the trench and measuring a depth of the trench;
   forming a gate pattern in the trench, wherein the gate pattern fills a lower region of the trench and exposes an upper region of the trench;
   obtaining a second measurement data from the gate pattern using an X-ray fluorescence analysis instrument;
   obtaining a first volume of the trench using the first measurement data;
   obtaining a second volume of the gate pattern using the second measurement data;
   obtaining a measurement target parameter using a difference between the first and second volumes, wherein the measurement target parameter is a distance between a top surface of the gate pattern and a top surface of the substrate; and
   examining whether the measurement target parameter is within an allowed range.

2. The method of claim 1, wherein
   the first measurement data is obtained using a non-destructive testing method,
   the width of the trench is measured by the scanning electron microscope (SEM)instrument, and
   the depth of the trench is measured by the optical scatterometry instrument.

3. The method of claim 1, wherein the obtaining the second measurement data comprises measuring mass of an element contained in the gate pattern.

4. The method of claim 3, wherein the second measurement data is obtained using a non-destructive testing method, and
   the mass of the element contained in the gate pattern is measured by the X-ray fluorescence analysis instrument.

5. The method of claim 3, wherein the obtaining the measurement target parameter comprises operating a calculation module included in a computer system,
   the calculation module is configured to calculate the first volume, the second volume, and the measurement target parameter, the first volume being calculated by multiplying the width of the trench, the depth of the trench, and a first constant, the second volume being calculated by multiplying the mass of the element contained in the gate pattern by a second constant, and the measurement target parameter being calculated by dividing a third volume, which is obtained by subtracting the second volume from the first volume, by multiplication of the width of the trench and the first constant.

6. The method of claim 5, wherein the obtaining of the measurement target parameter further comprises operating a verification module included in the computer system,
   the verification module is configured to determine the first and second constants to reduce an error between the measurement target parameter calculated by the calculation module and reference data.

7. The method of claim 1, wherein the forming of the gate pattern comprises:
   forming a gate layer on the substrate to fill the trench; and
   etching the gate layer,
   wherein if the examining determines the measurement target parameter is smaller than the allowed range, repeating the etching the gate layer.

8. A method of determining a physical parameter of a semiconductor device under manufacture, comprising:
   performing non-destructive measuring of at least a first physical parameter and a second physical parameter of structures in the semiconductor device under manufacture using a scanning electron microscope, an optical scatterometry instrument, and an X-ray fluorescence analysis instrument, each of the scanning electron microscope, the optical scatterometry instrument, and the X-ray fluorescence analysis instrument including a separate chuck configured to support the semiconductor device, the first physical parameter including a measurement of a recess region, and the second physical parameter including a measurement of a conductive pattern filling a portion of the recess region; and
   determining a third physical parameter of the structures based on data generated from the performing of the non-destructive measuring.

* * * * *